(12) United States Patent
Gulati et al.

(10) Patent No.: US 8,980,222 B2
(45) Date of Patent: Mar. 17, 2015

(54) DIAGNOSTIC USE OF ENDOTHELIN $ET_B$ RECEPTOR AGONISTS AND $ET_A$ RECEPTOR ANTAGONISTS IN TUMOR IMAGING

(75) Inventors: Anil Gulati, Naperville, IL (US); Kartike Gulati, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1747 days.

(21) Appl. No.: 11/791,131

(22) PCT Filed: Nov. 21, 2005

(86) PCT No.: PCT/US2005/042258
§ 371 (c)(1),
(2), (4) Date: Jun. 18, 2008

(87) PCT Pub. No.: WO2006/057988
PCT Pub. Date: Jun. 1, 2006

(65) Prior Publication Data
US 2008/0260634 A1 Oct. 23, 2008

Related U.S. Application Data

(60) Provisional application No. 60/629,923, filed on Nov. 22, 2004.

(51) Int. Cl.
*A61K 49/00* (2006.01)

(52) U.S. Cl.
CPC .................................. *A61K 49/0002* (2013.01)
USPC .......................................................... 424/9.1

(58) Field of Classification Search
None
See application file for complete search history.

(56) References Cited

U.S. PATENT DOCUMENTS

| 2003/0104976 A1* | 6/2003 | Davar et al. | 514/1 |
| 2004/0138121 A1* | 7/2004 | Gulati | 514/12 |

FOREIGN PATENT DOCUMENTS

| WO | WO-2004/037235 | 5/2004 |

OTHER PUBLICATIONS

Ishizuka T, Takamizawa-Matsumoto M, Suzuki K, Kurita A. Endothelin-1 enhances vascular cell adhesion molecule-1 expression in tumor necrosis factor alpha-stimulated vascular endothelial cells. 1999 Eur. J. Pharmacol. 369: 237-245.*

Sardanelli F, Calabrese M, Zandrino F, Melani E, Parodi R, Imperiale A, Massa T, Parodi G, Canavese G. Dynamic helical CT of breast tumors. 1998 J. Comput. Assist. Tomogr. 22: 398-407.*
Bell KM, Chaplin DJ, Poole BA, Prise VE, Tozer GM. Modification of blood flow in the HSN tumour and normal tissues of the rat by the endothelin ET(B) receptor agonist, IRL 1620. 1999 Int. J. Cancer 80: 295-302.*
Harvey C, Dooher A, Morgan J, Blomley M, Dawson P. Imaging of tumour therapy responses by dynamic CT. 1999 Eur. J. Radiol. 30: 221-226.*
Recht A, Come SE, Henderson IC, Gelman RS, Silver B, Hayes DF, Shulman LN, Harris JR. The sequencing of chemotherapy and radiation therapy after conservative surgery for early-stage breast cancer. 1996 N. Engl. J. Med. 334: 1356-1361.*
Brasch et al. Assessing tumor angiogenesis using macromolecular MR imaging contrast media. 1997 J. Magn. Reson. Imaging 7: 68-74.*
Bell et al., "Effect of Endothelin-1 and Sarafotoxin S6c on Blood Flow in a Rat Tumor," Journal of Cardiovascular Pharmacology, 26(Suppl. 3)S222-S225 (1995).
Bomber et al., "Propranolol Hydrochloride Enchancement of Tumor Perfusion and Uptake of Gallium-67 in a Mouse Sarcoma," J Nucl Med 27:243-245 (1986).
Graf, et al., "Determination of Optimal Time Window for Liver Scanning with CT during Arterial Portography," Radiology, 190:43-47 (1994).
International Search Report in PCT/US2005/042258 dated May 31, 2007.
Muruganandham, et al., "Diltazem Enhances Tumor Blood Flow: MRI Study in a Murine Tumor," Int. J. Radiation Oncology Biol. Phys., 34(2) pp. 413-421 (1999).
Rai et al., "Evidence for the Involvement of $ET_B$ Receptors in ET-1-Induced Changes in Blood Flow to the Rat Tumor," Cancer Chemother Pharmacol, 51:21-28 (2003).
Rajeshkumar et al., "Endothelin B Receptor Receptor Agonist, IRL 1260, Increases Blood Perfusion and Enhances Paclitaxel Delivery to Tumor," Proceedings of the Annual Meeting of the American Associate for Cancer Research, New York, NY, 46 p. 5741, 2005.
Smyth et al., "Use of Vasoactive Agents to Increase Tumor Perfusion and the Antitumor Efficacy of Drug-Monoclonal Antibody Conjugates," JNCI, 79(6) pp. 1367-1373 (1987).
Sonveaux, "Endothelin-1 Is a Critical Mediator of Myogenic Tone in Tumor Arterioles: Implications for Cancer Treatment," Cancer Research, 64, pp. 3209-3214 (2004).
Wu, "Recent Discovery and Development of Endothelin Receptor Antagonists," Exp. Opin. Ther. Patents, 10(11):1653-1668 (2000).

* cited by examiner

*Primary Examiner* — Michael G Hartley
*Assistant Examiner* — Jennifer Lamberski
(74) *Attorney, Agent, or Firm* — Marshall, Gerstein & Borun LLP

(57) ABSTRACT

Methods of imaging tumors are disclosed. The methods utilize an endothelin $ET_B$ receptor agonist or an endothelin $ET_A$ receptor antagonist, in combination with an imaging agent, to detect a tumor in mammals, including humans.

8 Claims, 8 Drawing Sheets

DIAGNOSTIC USE OF ENDOTHELIN $ET_B$ RECEPTOR AGONISTS AND $ET_A$ RECEPTOR ANTAGONISTS IN TUMOR IMAGING

CROSS-REFERENCE TO RELATED APPLICATIONS

This is the U.S. national phase application of International Application No. PCT/US2005/042258, filed Nov. 21, 2005, which claims the benefit of U.S. Provisional Patent Application No. 60/629,923, filed Nov. 22, 2004.

FIELD OF THE INVENTION

The present invention relates to methods of imaging tumors, such as breast tumors, in a mammal, either by administration of an effective amount of an endothelin $ET_B$ receptor agonist, or an endothelin $ET_A$ receptor antagonist, in combination with an imaging agent.

BACKGROUND OF THE INVENTION

Cancer is the second leading cause of death in the United States. The National Cancer Institute estimates that about eight million Americans have a history of cancer. In the United States, about 1 million new cancer cases are diagnosed each year, and about 500,000 individuals die of cancer each year.

However, between 1992 and 1998, the cancer death rate in the United States fell by 1.1%. This reduction is at least partially attributed to an early detection and diagnosis of a cancer, and an earlier treatment regimen, which can lead to a greater likelihood of cure. Medical imaging has become vital in the early detection and diagnosis of cancer, which may allow a cancer treatment to begin before the cancer metastasizes to other body tissues and organs. In many cases, if a cancer is detected sufficiently early, an early treatment can lead to a complete cure.

Cancer research and diagnosis both are critically dependent on imaging technologies. Imaging advances already permit remarkable accuracy in (a) detecting whether a tumor has invaded vital tissue, grown around blood vessels, or spread to distant organs; (b) allowing physicians to monitor patient progress without the need for biopsies; and (c) allowing a precise delivery of tumor-destroying agents to the tumor site. Computed tomography (CT) imaging, magnetic resonance (MR) imaging, mammography, nuclear medicine (NM) imaging, ultrasound (US) imaging, and X-ray imaging are important imaging tools in achieving these goals.

Pharmaceutical compounds administered by intravenous, oral, or rectal routes often are termed "contrast agents," and sometimes referred to as a "dye." A contrast agent is used to make specific organs, blood vessels, and/or tissues "stand out" with more image contrast in order to more definitively reveal the presence of a disease or injury. Thus, a contrast agent high-lights specific areas of the resultant image, or "dyes" the image. The use of contrast agents greatly improves the ability of imaging techniques in the detection and diagnosis of cancer, and improves the prognosis of a recovery by the patient. For example, gadolinium-DTPA enhanced MRI and CT, with or without a contrast agent, are commonly used in the detection of solid tumors.

The present invention is directed to the use of an endothelin $ET_B$ receptor agonist or an endothelin $ET_A$ receptor antagonist, in combination with an imaging agent, to enhance a diagnostic method of detecting a tumor.

SUMMARY OF THE INVENTION

The present invention is directed to administration of an effective amount of an endothelin $ET_B$ receptor agonist and an imaging agent to an individual in a diagnostic assay for a tumor. The present invention also is directed to administration of an effective amount of an endothelin $ET_A$ receptor antagonist and an imaging agent to an individual in a diagnostic assay for a tumor, such as a solid tumor.

Tumors need a blood supply to grow, and, therefore, have a well-developed vasculature. Endothelin (ET) is a powerful regulator of blood flow. $ET_A$ receptors have been found to be vasoconstrictors, and $ET_B$ receptors have been found to be vasodilators. It also has been demonstrated that tumor tissue, like a breast tumor, has abundant $ET_B$ receptors, and that an $ET_B$ receptor agonist can increase blood flow to a tumor because of its ability to vasodilate. In addition, because an $ET_A$ receptors are vasoconstrictive, an $ET_A$ receptor antagonist likewise can increase blood flow to a tumor.

Therefore, because $ET_B$ receptors are vasodilators, an $ET_B$ receptor agonist, in combination with an imaging agent, is useful in the detection and diagnosis of a tumor, such as those found in breast cancer. In this embodiment, the $ET_B$ receptor agonist more effectively delivers the imaging agent to the tumor resulting in an enhanced diagnostic assay. More particularly, an enhanced imaging allows detection of a smaller tumor, such that treatment of a malignant tumor can be initiated at a time that improves the probabilities of patient recovery and survival. Enhanced imaging also allows medical personnel to differentiate a malignant tumor from a benign tumor.

Accordingly, one aspect of the present invention is to provide a diagnostic method of detecting tumors comprising administering to a mammal in need thereof an effective amount of an endothelin B ($ET_B$) receptor agonist and an imaging agent.

Another aspect of the present invention is to provide a composition comprising an $ET_B$ receptor agonist. The present invention also is directed to compositions containing an $ET_B$ receptor agonist, and to methods of administering the composition in conjunction with an imaging agent, to detect tumors. An especially important aspect of this method is an ability to detect the tumor at an earlier stage, i.e., when the tumor is smaller, than administration of the imaging agent alone.

Still another aspect of the present invention is to provide a composition comprising an $ET_B$ receptor agonist, an imaging agent useful in the detection of a tumor, and an excipient.

Still another aspect of the present invention is to provide a diagnostic method of detecting tumors comprising administering to a mammal in need thereof an effective amount of an endothelin A receptor antagonist and an imaging agent. The endothelin A receptor antagonist can be a specific endothelin A ($ET_A$) receptor antagonist, a mixed endothelin A/B ($ET_{A/B}$) receptor antagonist, or a mixture thereof (hereafter collectively referred to as an $ET_A$ receptor antagonist). Preferably, the $ET_A$ receptor antagonist comprises a specific $ET_A$ receptor antagonist. The endothelin antagonist is used in conjunction with an imaging agent.

Another aspect of the present invention is to provide a composition comprising an $ET_A$ or an $ET_{A/B}$ receptor antagonist. The present invention also is directed to compositions containing an $ET_A$ receptor antagonist, and to methods of administering the composition, in conjunction with an imaging agent, to detect tumors. An especially important aspect of this method is an ability to detect the tumors at an earlier stage than administration of the imaging agent alone.

Another aspect of the present invention is to provide a composition comprising an $ET_A$ receptor antagonist, an imaging agent useful in the detection of a tumor, and an excipient.

Yet another aspect of the present invention is to provide an article of manufacture for human pharmaceutical use, comprising (a) a container, and (b1) a packaged composition comprising an $ET_B$ receptor agonist and, optionally, (b2) a packaged composition comprising an imaging agent useful in the detection of a tumor, and (c) a package insert containing directions for use of the composition or compositions administered simultaneously or sequentially, in a diagnostic method of detecting a tumor.

Another aspect of the present invention is to provide an article of manufacture for human pharmaceutical use, comprising (a) a container, (b1) a packaged composition comprising an $ET_A$ antagonist and, optionally, (b2) a packaged composition comprising an imaging agent useful in the detection of a tumor, and (c) a package insert containing directions for use of the composition or compositions, administered simultaneously or sequentially, in a diagnostic of detecting a tumor.

These and other novel aspects of the present invention will become apparent from the following detailed description of the preferred embodiments of the invention taken in conjunction with the figures.

DETAILED DESCRIPTION OF THE PREFERRED EMBODIMENTS

One pressing need in clinical oncology is to provide imaging agents capable of identifying tumors that are far smaller than possible with present-day technology, i.e., at a scale of 100,000 cells rather than 1,000,000 cells. Achieving this level of sensitivity requires an improved targeting of imaging agents and the generation of a larger imaging signal. The present invention is directed to a novel method of delivering imaging agents to a tumor, and thereby generate improved imaging signals.

Endothelins are involved in a variety of physiological functions, involving the cardiovascular, renal, pulmonary, endocrine, and central nervous systems. Endothelins exert their effects by binding to two distinct types of cell surface receptors, $ET_A$ and $ET_B$. $ET_A$ and $ET_B$ receptors located on vascular smooth muscle cells produce vasoconstriction, whereas $ET_B$ receptors present on endothelial cells mainly are vasodilators (Remuzzi et al., *Nat. Rev. Drug Discov.*, 1(12):986-1001 (2002)). The present invention is directed to a novel role of $ET_B$ receptor agonists or $ET_A$ receptor antagonists in increasing tumor delivery of imaging agents.

Figure 1:
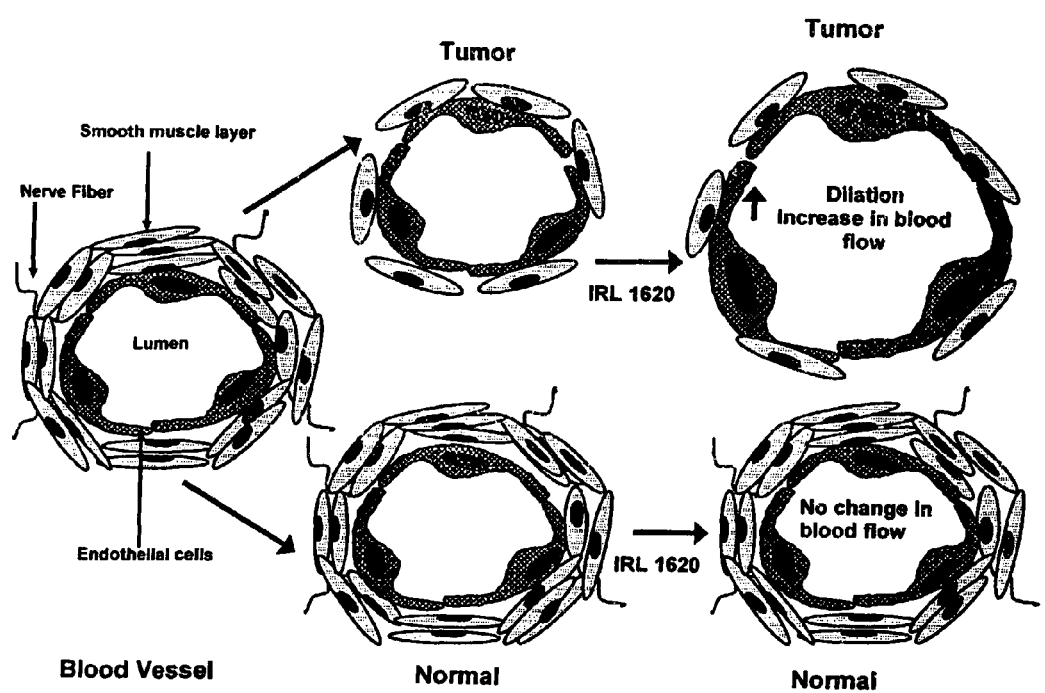
FIG. 1 is an illustration of the present invention showing an increase in blood flow in the presence of a tumor.

Blood vessels in the growing portion of tumors are devoid of smooth muscle covering and endothelial cells in tumor vessels proliferate rapidly (Helmlinger et al., *Nature*, 405 (6783):139-41 (2000)). Therefore, the angioarchitecture of a tumor is different from the normal vasculature (Carmeliet et al., *Nature*, 407 (6801):249-57 (2000)). Hence, administration of a selective $ET_B$ receptor agonist or $ET_A$ receptor antagonist should selectively increase tumor blood flow, as is illustrated in FIG. 1. Administration of imaging agents during the elevated tumor perfusion leads to enhanced accumulation of an imaging agent in the tumor tissue producing a sharper, brighter, and better image of the tumor.

The present invention, therefore, is directed to compositions and methods of detecting tumors, including breast tumors. In particular, the present invention is directed to pharmaceutical compositions comprising either (a) an $ET_B$ receptor agonist and, optionally, an imaging agent or (b) an $ET_A$ receptor antagonist, and optionally, an imaging agent.

In addition, the present invention is directed to articles of manufacture comprising an $ET_B$ receptor agonist and an imaging agent, packaged separately or together, and an insert having instructions for using these agents to detect a tumor.

The present invention further is directed to articles of manufacture comprising an $ET_A$ receptor antagonist and an optional imaging agent, packaged separately or together, and an insert having instructions for using these agents to detect a tumor.

One method disclosed herein utilizes an $ET_B$ receptor agonist and an imaging agent in the detection of a tumor. The agonist is administered with the imaging agent, simultaneously or sequentially, to a person in need thereof in a sufficient amount to enhance the imaging capabilities of the imaging agent.

Another method disclosed herein utilizes an $ET_A$ receptor antagonist and an imaging agent in the detection of a tumor. The antagonist is administered with the imaging agent, simultaneously or sequentially, to a person in need thereof in a sufficient amount to enhance the imaging capabilities of the imaging agent.

For the purposes of the invention disclosed herein, the term "treatment" includes preventing, retarding the progression of, shrinking, or eliminating a tumor. As such, the term "treatment" includes both medical therapeutic and/or prophylactic administration, as appropriate.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "prodrug" means compounds that trans-form rapidly in vivo to a compound useful in the invention, for example, by hydrolysis. A thorough discussion of prodrugs is provided in Higuchi et al., *Prodrugs as Novel Delivery Systems*, Vol. 14, of the A.C.S.D. Symposium Series, and in Roche (ed.), *Bioreversible Carriers in Drug Design*, American Pharmaceutical Association and Pergamon Press, 1987.

The development of tumor vasculature has been studied extensively. Tumors that grow beyond the size of a few millimeters require a constant nutrient supply and, therefore, have their own vascular bed and blood flow (4). Tumor blood vessels develop very differently from normal vasculature, and have different properties. Single layered epithelial cells are the first hastily formed tumor blood vessels. It has been suggested that these blood vessels are recruited when the tumor secretes certain growth factors, like VEGF, in response to hypoxic conditions (5). These newly formed tumor blood vessels do not have a smooth muscle layer or innervation (6-8). Tumors also incorporate mature blood vessels that possess all their autoregulatory functions (6). Normal tissue vascular tone is governed by a host of endogenous factors, like $H^+$, $K^+$, $Ca^{2+}$, $pO_2$, $pCO_2$, and nitric oxide (NO), as well as other regulatory substances, like endothelin (ET-1) (9, 10).

Blood vessels in the growing part of tumors are devoid of smooth muscle covering and a fraction of endothelial cells in tumor vessels proliferate rapidly (14-17). It is theorized, but not relied upon herein, that these rapidly proliferating endothelial cells respond to $ET_B$ receptor agonists. Furthermore, the endothelial cells are considered genetically stable and, therefore, may not develop drug resistance against $ET_B$ agonists.

Endothelins (ETs) are vasoactive substances that act on subtypes of receptors. At least three forms of ET receptors exist, and are known as $ET_A$, $ET_B$, and $ET_C$. $ET_A$ has a higher affinity for ET-1, but $ET_B$ has equal affinity for both ET-1 and ET-3 (11, 26, 27). $ET_A$ receptors expressed on the smooth muscle cells are responsible for vasoconstriction. $ET_B$ receptors located on endothelial cells produce vasodilatation (1, 11-13).

ET-1 is a powerful vasoconstrictor (25). ET-1 belongs to a family of peptides approximately 21 amino acids long. ET-1 has complex cardiovascular effects. When administered to anesthetized and ventilated rats, an immediate decrease followed by a sustained increase in blood pressure is observed (28). ET-1 administration results in an increase in blood flow to skin tumors, possibly due to the vasodilatory actions of $ET_B$ receptors (29). Similar results in blood flow to the breast tumor of rats are demonstrated because of an increase in ET-1 and $ET_B$ receptors in breast tumors. Because $ET_A$ is responsible for vasoconstrictor responses, $ET_A$ receptor antagonists similarly can be used to dilate the blood vessels. Accordingly, endothelin $ET_B$ receptor agonists and $ET_A$ receptor antagonists can be used to transiently dilate tumor blood vessels and enhance the selective delivery of imaging agents to the tumor tissue and, therefore, aid in diagnosis of a cancer and in monitoring the progression of a cancer treatment.

It has been found that $ET_B$ receptor agonists selectively improve tumor perfusion (1) and enhance the delivery of antineoplastic agents to a solid tumor (2, 3). A transient window of elevated perfusion provides sufficient opportunity for an enhanced accumulation of paclitaxel in the tumor. Data shows that an $ET_B$ receptor agonist did not change the blood plasma pharmacokinetic profile of paclitaxel, and significantly increased (453%) the concentration of paclitaxel in the tumor. Selective targeting of such chemotherapeutic agents to the tumor tissue can increase chemotherapeutic efficiency, and can diminish the risk of adverse effects without compromising chemotherapeutic efficacy.

Endothelin is a vasoactive substance known to modulate blood flow and also has mitogenic properties. Endothelin is present in large concentrations in breast carcinoma tissues compared to normal breast tissue. It also has been shown that a subtype of endothelin receptor ($ET_B$) also is increased in breast cancer. See WO 2004/037235 incorporated herein by reference. Endothelin acts on $ET_B$ receptors to produce vascular dilation and increase in blood flow to the breast tumor tissue.

Because endothelin and $ET_B$ receptors are overexpressed in breast cancer, an $ET_B$ receptor agonist that selectively increases blood supply to the tumor can increase the delivery and efficacy of an imaging agent. Therefore, $ET_B$ receptor agonists can selectively increase the delivery of imaging agents, like a contrast agent, to a tumor, and thereby increase the efficacy of the imaging agent. An increase in imaging agent efficacy allows an earlier detection of a tumor, and an earlier onset of a therapeutic regimen.

In addition, $ET_A$ receptors are vasoconstrictive. Therefore, administration of an $ET_A$ receptor antagonist will lead to vasodilation, and to a selective increase in the delivery of an imaging agent to a tumor.

More particularly, tumor blood supply has become a target of cancer detection and therapy. Several vasoactive substances are known to modulate blood flow including endothelin-1 (ET-1). ET-1 is present in large concentrations in breast carcinoma tissues (i.e., 11.95 pg/mg tissue) compared to normal breast tissue (i.e., 0.12 pg/mg tissue) (Kojima et al., *Surg. Oncol.*, 4(6): 309-315 (1995); Kurbel et al., *Med. Hypotheses*, 52(4): 329-333 (1999); Patel et al., *Mol. Cell Endocrinol.*, 126(2):143-151 (1997); Yamashita et al., *Cancer Res.*, 52(14):4046-4049 (1992); Yamashita et al., *Res. Commun. Chem. Pathol. Pharmacol.*, 74(3):363-369 (1991).

Studies have shown that ET-1, ET-3, and $ET_B$ receptor expression is increased in breast cancer (grade III, strong staining compared to negative staining in controls) (Alanen et al., *Histopathology*, 36(2):161-167 (2000)). It also has been found that ET-1 produces an increase in blood flow to the breast tumor by stimulating $ET_B$ receptors. BQ788, an $ET_B$ receptor antagonist, completely blocked ET-1 induced increase in tumor blood flow. Because breast tumor tissue has enhanced $ET_B$ receptor expression, an $ET_B$ receptor agonist or an $ET_A$ receptor antagonist can be used to increase blood flow to the breast tumor tissue.

Accordingly, administration of an $ET_B$ receptor agonist or an $ET_A$ receptor antagonist in combination with an imaging agent increases blood flow to a tumor and more selectively delivers the imaging agent to the tumor. Detection of a tumor and a cancer diagnosis, therefore, is enhanced.

In accordance with the present invention, an endothelin $ET_B$ receptor agonist or an $ET_A$ receptor antagonist can be used to transiently dilate the tumor blood vessels and enhance the selective delivery of imaging agent, including contrast media and dyes, to tumor tissue, and, therefore, enhance detection of a tumor and improve diagnoses of cancers. For example, enhancement of tumor image can be achieved by using an $ET_B$ receptor agonist or an $ET_A$ receptor antagonist to increase the perfusion of gadolinium-DEPA, iodinated contrast media, echo contrast agents, and ultrasound contrast agents. In particular, the use of an echo contrast agent improves the diagnostic ability of ultrasonography to detect and differentiate liver tumors. $ET_B$ receptor agonists and $ET_A$ receptor antagonists can further improve the diagnostic ability of ultrasonography by selectively improving the perfusion of contrast agents to tumor tissue.

Another example is ultrasound, wherein contrast agents originally were introduced to enhance the Doppler signals when detecting vessels with low velocity flow or when imaging conditions were suboptimal. Contrast agents showed additional properties. In particular, it was discovered that a parenchymal enhancement phase in the liver followed the enhancement of the blood pool. Contrast agents, therefore, have made ultrasound scanning more accurate in detection and characterization of focal hepatic lesions, and sensitivity is now comparable with CT and MRI scanning. The accuracy of these techniques can be further enhanced by selectively increasing tumor perfusion by administering an $ET_B$ receptor agonist or an $ET_A$ receptor antagonist with the contrast agent, either simultaneously or sequentially.

An important aspect of an enhanced ability to detect a tumor is that a previously undetectable tumor may be detected, which would lead to an earlier diagnosis and earlier treatment. With an earlier treatment, the prospects for a successful treatment are increased. Another important aspect of the present invention is that enhanced imaging may confirm that a tumor is or is not present. Such confirmation may obviate additional tests, including intrusive surgical-type tests, to confirm the presence or absence of a tumor.

Administration of an $ET_B$ receptor agonist or $ET_A$ receptor antagonist in combination with an imaging agent can be used to detect numerous tumors, including, but not limited to, ovarian cancer, colon carcinoma, breast cancer, brain cancer, liver cancer, colorectal cancer, metastatic colorectal cancer, metastatic breast cancer, esophageal, gastric, or small bowel cancer, hepatobiliary cancer, pancreatic cancer, lymphoma, bladder cancer, germ cell/testicular tumors, kidney cancer, prostate cancer, genitourinary cancer, head and neck cancer, nonsmall cell lung cancer, small cell lung cancer, other lung cancers, melanoma, and pediatric solid tumors.

In one embodiment of the present invention, a tumor is detected using an $ET_B$ receptor agonist in conjunction with an imaging agent. In this method, the $ET_B$ receptor agonist increases blood flow in the tumor. It is theorized, but not relied upon herein, that the agonists stimulate $ET_B$ receptors and dilate tumor blood vessels, thereby increasing delivery of the imaging agent to the tumor. The $ET_B$ agonist, therefore, provides a more selective target for the imaging agent and enhances the imaging effect of the imaging agent.

A preferred $ET_B$ agonist is selective for $ET_B$ receptors. $ET_B$ receptor agonists useful in the present invention include, but are not limited, to, ET-1, ET-2, ET-3, BQ-3020, IRL-1620, sarafotoxin S6c, [Ala$^{1, 3, 11, 15}$]-ET-1, and mixtures thereof.

In another embodiment of the present invention, a tumor is detected using an $ET_A$ receptor antagonist in conjunction with an imaging agent. In this method, the $ET_A$ receptor antagonist also increases blood flow in a tumor. It is theorized, but not relied upon herein, that the antagonists inhibit $ET_A$ receptors and dilate tumor blood vessels, thereby increasing delivery of the imaging agent to the tumor.

$ET_A$ receptor antagonists useful in the present invention can be selective $ET_A$ antagonists or balanced $ET_A/ET_B$ antagonists. $ET_A$ receptor antagonists, and balanced $ET_A/ET_B$ antagonists, useful in the treatment and/or prevention of solid tumors are set forth in Appendices A and B herein. Additional useful endothelin antagonists can be found in U.S. Patent Application Publication No. US 2002/0082285 A1, incorporated herein by reference.

Examples of $ET_A$ antagonists useful in the present invention include, but are not limited to, atrasentan, sitaxsentan, clazosentan, tezosentan, sulfisoxazole, BQ-123, BQ-610, SB 209670, SB 217242, FR-139317, PD-164333, PD-151242, TTA-386, JKC-301, JKC-302, BE-18257A, BE-18257B, BQ-485, TBC-11251, PD 156707, A-127722, LU 135252, BMS182874, BMS193884, and mixtures thereof.

In addition to a conventional antagonist, a compound that inhibits the formation of endogenous endothelin also can be used as the endothelin antagonist in the present invention. Such compounds are useful because they prevent endothelin formation and, therefore, decrease the activity of endothelin receptors. One class of such compounds is the endothelin converting enzyme (ECE) inhibitors. Useful ECE inhibitors include, but are not limited to, CGS34225 (i.e., N-((1-((2-(S)-(acetylthio)-1-oxopentyl)-amino)-1-cyclopentyl)-carbonyl-S-4-phenylphenyl-alanine methyl ester) and phosphoramidon (i.e., N-(1-rhamnopyranosyloxyhydroxyphosphinyl)-Leu-Trp).

In these embodiments, the $ET_B$ receptor agonist or $ET_A$ receptor antagonist is used in conjunction with an imaging agent. The $ET_B$ receptor agonist or $ET_A$ receptor antagonist enhances the imaging capabilities of the imaging agent by helping to concentrate the imaging agent at the tumor site. Accordingly, an improved diagnostic assay for a tumor is achieved.

Imaging agents that can be used in the present method include, but are not limited to:

X-ray contrast agents;
Main ionic contrast media, such as acetrizoic acid derivatives, diatrizoic acid derivatives, iothalamic acid derivatives, ioxithalamic acid derivatives, metrizoic acid derivatives, iodamide, lypophylic agents, aliphatic acid salts, iodipamide, ioglycamic acid;
Dimeric ionic contrast agents;
Ioxaglic acid derivatives;
Main nonionic contrast media, such as metrizamide, iopamidol, iohexol, iopromide, iobitridol, iomeprol, iopentol, ioversol, ioxilan;
Main nonionic dimeric contrast media, such as iodixanol, iotrolan;
Magnetic resonance imaging (MRI) contrast agents, such as gadolinium and manganese derivatives;
Superparamagnetic iron oxide particles;
Ultrasound contrast agents;
Nuclear imaging agents;
Radioimmunopharmaceuticals;
Growth factors;
Growth inhibitors;
Diagnostic radiopharmaceuticals;
Radiopharmaceutical agents based on cyclo-oxygenase-2 (COX-2) inhibitors that target the COX-2 enzyme, which is crucial to prostaglandin synthesis, for imaging therapeutic responses to lung, breast, and colorectal cancer treatment;
Immunoconjugates;
Perfluorocarbons (PFCs) and PFC emulsions as diagnostic contrast agents, including applications of FLUTEC™ PFC liquids and gases, Advanced Magnetics' proprietary colloidal superparamagnetic particle technology, Cytogen's proprietary enabling technology, Diatide's Techtide technology, Enzon's single chain antigen-binding technology, Immunomedics' antibody technology, Liposome Company's liposome technology, and NeoRx's "Painting the Target" technology;
Gas Encapsulation Technology for ultrasound contrast media, including Pharmacyclics' Texaphyrin technology regulatory bodies;
Amide-based macrocyclic ligands, including MRI agents gadolinium (III) complexes;
Potential MRI contrast agents including metal-containing compounds as contrast agents;
Magnetic gels as MRI contrast agents;
Bismuth nitrate;
Isovue;

Nonionic monomeric X-ray contrast agent;
Omnipaque (Amersham);
F-18 FDG (Syncor International);
Vascular (VTA) targeting agents for imaging a wide variety of cancer types; and
Nofetumomab, a fragment of a monoclonal antibody, that, when tagged with the radioisotope technetium, can detect a protein found on the surface of most small cell lung cancers.

In addition to the above, probes based on molecular discoveries are expanding the role of positron emission tomography (PET) in cancer treatment monitoring. In particular, compounds programmed to find and bind to cells having properties that indicate diseases, like cancer, heart disease, or Alzheimer's disease, are being synthesized. These compounds, also called probes, attach themselves to the biomarkers and "light up" under a standard imaging device, usually PET scanners. The images are computer processed using algorithms that can identify quantitative changes in the data.

Carbon-11 thymidine is the gold standard for tracking DNA proliferation. Although it is not practical for clinical use, work on this agent led to the development of F-18 fluorodeoxythymidine (FLT), F-18 2'-fluoro-5-methyl-1-beta-D-arabinofuranosyluracil (FMAU), and analogs having a longer half-life, such as iodine-124 iodo-2'-deoxyuridine (UdR). FLT's ability to detect changes in cell proliferation complements FDG's ability to measure glucose metabolism. FLT does not detect DNA division, the source of C-11 thymidine's predictive power, but proliferation marker Ki-67 histopathology tests have shown that FLT can track cancer cell division. This probe may gain acceptance for monitoring treatment because cancer cell proliferation slows almost immediately after the disease begins to respond positively to radio- or chemotherapy.

It has been demonstrated that ET-1 produces an increase in blood flow to tumors by stimulating $ET_B$ receptors. For example, BQ788, an $ET_B$ receptor antagonist, completely blocked an ET-1 induced increase in tumor blood flow. Similarly, an $ET_B$ receptor agonist or an $ET_A$ receptor antagonist increases blood supply to tumor tissue, thereby facilitating detection of a tumor by administration of an imaging agent. An $ET_B$ receptor agonist or an $ET_A$ receptor antagonist therefore can be used in combination with an imaging agent in a diagnostic method of detecting a tumor, or in a method of monitoring the progress of a cancer treatment. $ET_B$ receptor agonists and $ET_A$ receptor antagonists that selectively increase blood supply to a tumor therefore can increase the selective delivery of an imaging agent to a tumor, and efficacy of the imaging agent, which allows the detection of small tumors previously undetectable using the imaging agent. Therefore, an $ET_B$ receptor agonist or an $ET_A$ receptor antagonist enhances the ability of an imaging agent to detect a tumor.

Materials and Methods
Animals

Female Sprague Dawley rats (Harlan Co., Madison, Wis.) weighing 180-200 grams (g) were used. All animals were housed, three to a cage, in a temperature controlled room (23±1° C.), humidity (50±10%), and artificial light (0600-1800 hr). The animals were given food and water ad libitum. The experiments were conducted after the animals had been acclimatized to the environment for at least four days.

Drugs

N-methylnitrosourea (MNU) was purchased from Ash Stevens Inc., Detroit, Mich. BQ788 (N-cis-2,6-dimethylpiperidinocarbonyl-L-gamma-methylleucyl-D-1-methoxycarbonyltrptophanyl-D-Nle), IRL-1620, and Endothelin-1 (ET-1) were obtained from American Peptide Company Inc., Sunnyvale, Calif. BQ788 was dissolved in saline and ET-1 was dissolved in 0.1% albumin.

Chemically induced rat mammary carcinogenesis commonly is achieved by administration of 7,12-dimethylbenzene(a)anthracene (DMBA) (18) or N-methylnitrosourea (MNU) (18). Tumors induced by DMBA or MNU have different morphological characteristics. Tumors induced by MNU are more localized at the breast and are less like to metastasize (19). Therefore, in the present study, MNU was chosen as the chemical agent for the specific induction of breast tumors in rats. These tumors can be benign with fibroadenomas and papillomas, or the tumors can be malignant (20).

Rats have six pairs of mammary glands, one in the cervical region, two in the thoracic, one in the abdominal, and two in the ingual regions (20, 21). Virgin rats treated with MNU develop more tumors in the thoracic region than the abdominal region (22).

MNU or saline treatments were carried out as intraperitoneal injections three months prior to the study. Rats were regularly palpated from four weeks after onset of the treatments. When the tumors reached an optimal size (i.e., 4-8 mm in diameter), the experiments were begun. Systemic hemodynamic and regional circulation parameters were determined at baseline, 30, 60, and 120 minutes after initiating ET-1 (50 ng/kg/min) infusion. Because ET-1 infusion was performed for 30 minutes, the 30-minute data shows the effect of ET-1, and the 60- and 120-minute data indicates the duration of ET-1 effect.

Blood perfusion to the mammary gland of the rats was measured using laser Doppler flowmetry as described in literature procedures (23, 24). The animals were shaved around the nipples. The skin surrounding the mammary glands was dissected out as a lambeau about 6 cm wide and 4 cm long. A standard model fiber optic probe was applied to the surface of the lambeau, and secured to the tissue by double stick tape. The lambeau was placed in a metal holder and taped down to prevent movement, then connected to a Periflux PF2b 4000 Laser Doppler Flowmetry (Perimed KB, Stockholm, Sweden). The time constant was set at 1.5 seconds and the bandwidth was set at 4 KHz.

All data are presented as mean±SEM. Data were analyzed using analysis of variance followed by Duncan's test. A level of $p<0.05$ was considered significant.

Results

Effect of IRL-1620 on Breast Tumor Perfusion

IRL-1620, a highly selective $ET_B$ receptor agonist (i.e., 120,000-fold more selective to $ET_B$ compared to $ET_A$ receptors) was found to be the most effective agent to enhance blood flow to the tumor (Table 1). In a previous study, IRL-1620 was found to transiently dilate tumor blood vessels, improve tumor blood perfusion, and enhance delivery of chemotherapeutic agents to the tumor tissue (N. V. Rajeshkumar et al., *Breast Cancer Research and Treatment Online*, October 22:1-11 (2005)).

TABLE 1

Effect of various ET agonists on tumor blood perfusion measured using Laser Doppler Flowmetry

| $ET_B$ receptor agonist | Binding affinity (Ratio) $ET_A:ET_B$ | Maximal increase in tumor perfusion (%) |
|---|---|---|
| ET-1 | 1:1 | 46.19 |
| ET-3 | 1:3 | 47.99 |
| 4 Ala ET-1 | 1:1700 | 53.96 |
| IRL-1620 | 1:120,000 | 250.62 |

A preclinical model of MNU-induced primary autochthonous mammary tumor was used in the following studies. This tumor model of breast cancer offers several advantages over other models (Rai et al., *Cancer Chemother. Parmaacol.*, 51(1):21-8 (2003)). Virgin female Sprague Dawley rats were used for the study. At 48 days of age, rats received a single injection of N-methyl nitrosourea (MNU; 50 mg/kg, i.v.). Eighty percent of the animals developed tumors two months after MNU injection and 10% of total rats may die or loose weight due to MNU injection or develop a tumor after several months. Tumor appearance and location is monitored by manual mammary gland palpation and the tumor diameter is measured with a digital caliper. Rats with a tumor volume of 200-500 mm$^3$ were selected for the experiments.

Transient, Selective Enhancement of Blood Supply to Breast Tumor

Several ET agonists, i.e., ET-1 (equal affinity for $ET_A$ and $ET_B$ receptors), ET-3 (three times more selective for $ET_B$ receptors than $ET_A$ receptors), 4-Ala ET-1 (1700 times more selective for $ET_B$ receptors than $ET_A$ receptors (Saeki et al., *Biochem Biophys Res Commun*, 179(1):286-92 (1991)), and IRL-1620 (120,000-fold more selective for $ET_B$ receptors compared to $ET_A$ receptors (Takai et al., *Biochem Biophys Res Commun*, 184(2):953-9 (1992)) were tested, and it was found that the most selective $ET_B$ receptor agonist, IRL-1620, produced a maximal increase in breast tumor blood perfusion (Table 1). The effect of IRL-1620 (1, 3 and 9 nmol/kg, iv) on breast tumor perfusion in rats is shown in FIG. 2.

Figure 2:
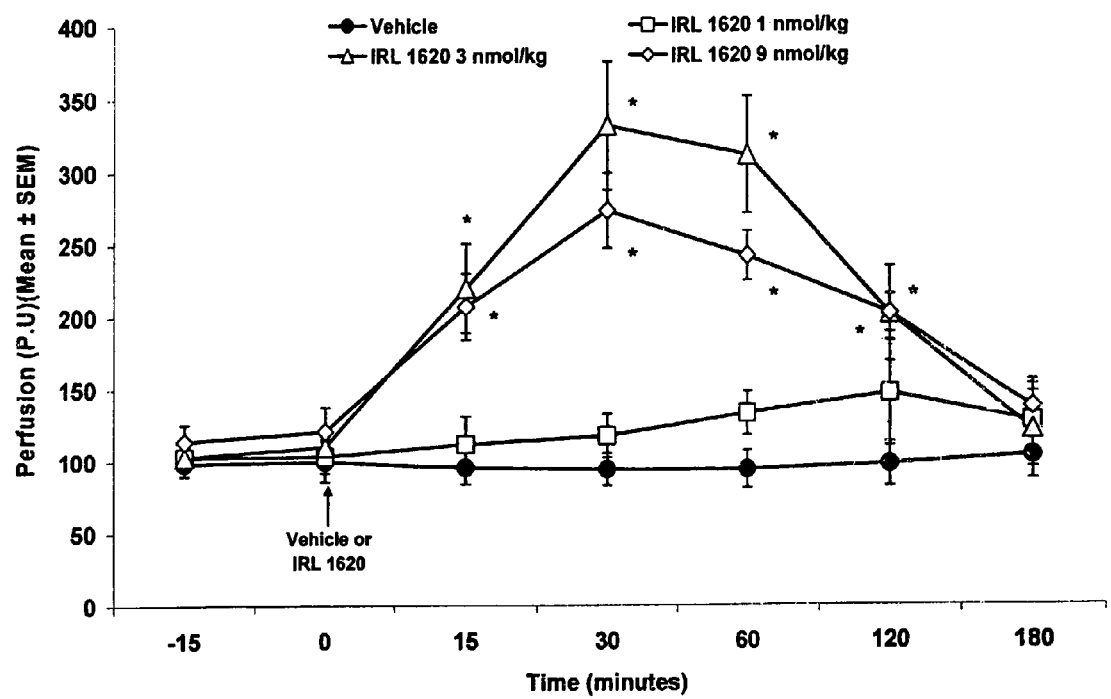
FIG. 2 contains plots showing the effect of IRL-1620 on breast cancer.

FIG. 2 illustrates the effect of IRL-1620 on breast tumor perfusion (N=5/group). Breast tumor-bearing rats were anesthetized and mammary tumor perfusion was recorded using a Laser Doppler Flowmetry for three hours. A 15-minute stable baseline recording was obtained before the administration of saline or IRL-1620 1, 3, or 9 nmol/kg via the tail vein in a final volume of 0.2 ml. Tumor perfusion was recorded for three hours (*p<0.001 compared to vehicle-treated rats).

Administration of IRL-1620 (3 and 9 nmol/kg) produced a significant increase in tumor perfusion compared to baseline and vehicle treated rats. It was found that 1 nmol/kg dose of IRL-1620 did not produce any effect and 3 nmol/kg dose produced a maximal increase in tumor perfusion (203.5%), which was more than that of 9 nmol/kg (140.5%). Therefore, 3 nmol/kg dose of IRL-1620 was selected for delivery of imaging agent to the tumor.

The involvement of $ET_B$ receptors in the action of IRL-1620 was confirmed by treating animals with BQ 788, a highly selective $ET_B$ receptor antagonist. It was found that in rats treated with BQ 788, the effect of IRL-1620 on tumor blood perfusion was completely blocked (FIG. 3).

Figure 3:
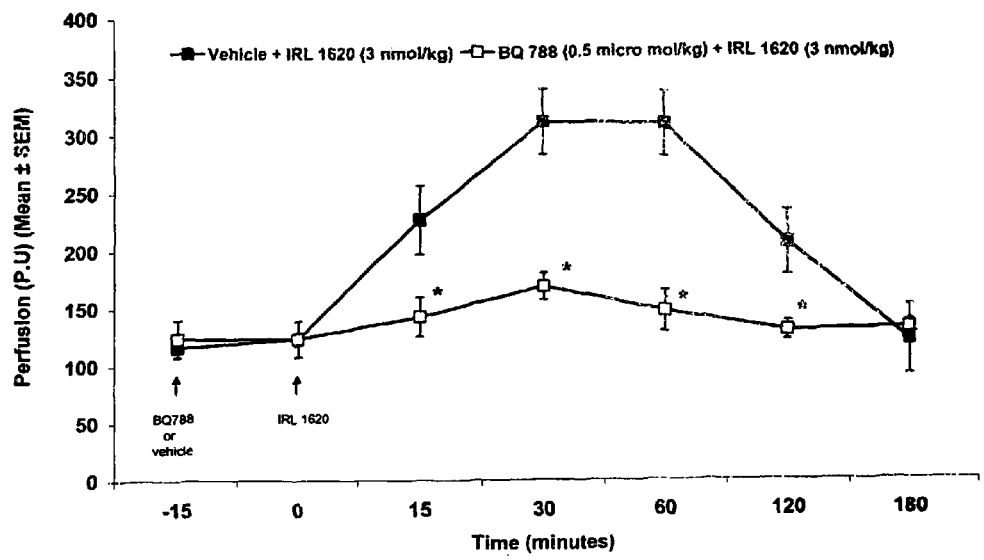
FIG. 3 contains plots showing the inhibitory effect of BQ 788 on IRL-1620 induced tumor perfusion.

FIG. 3 shows the inhibitory effect of BQ 788 on IRL-1620 (3 nmol/kg) induced tumor perfusion (N=4/group). Animals received BQ 788 (0.5 μg/kg) or saline via tail vein 15 minutes before the administration of IRL-1620 (3 nmol/kg) and tumor perfusion was recorded for three hours (*p<0.001 compared to BQ 788-administered rats). Studies also were conducted to determine the effect of IRL-1620 on blood perfusion in normal mammary tissue. It was found that IRL-1620 (1, 3 and 9 nmol/kg) did not produce any effect on blood perfusion of normal mammary tissue, thereby demonstrating that an increase in blood perfusion by IRL-1620 does not occur in normal mammary tissue, but is specific to tumor tissue (FIG. 4).

Figure 4:
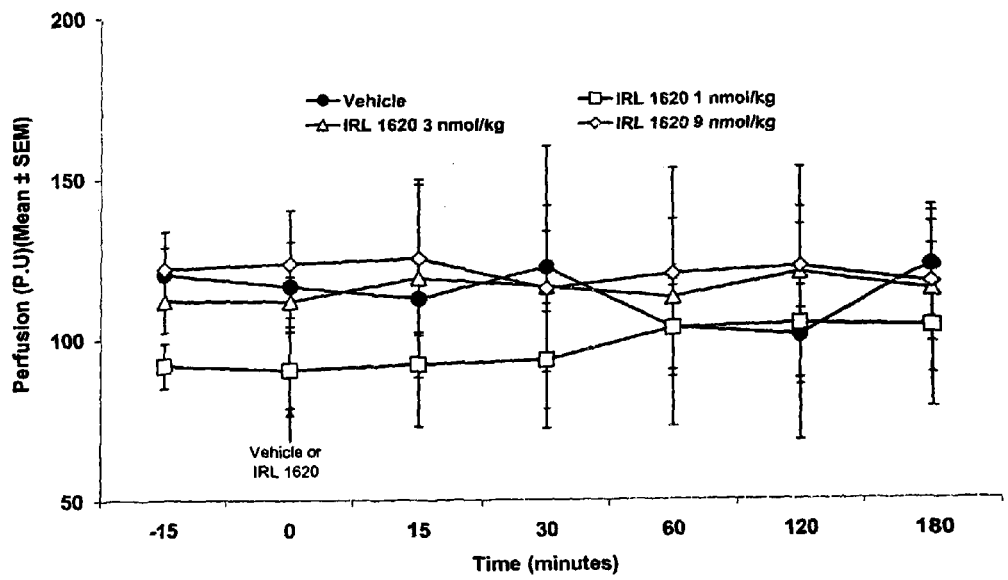
FIG. 4 contains plots showing the effect of IRL-1620 on breast perfusion of normal rats.

FIG. 4 shows the effect of IRL-1620 on breast perfusion of normal rats (N=4/group). Rats were anesthetized and mammary perfusion was recorded using a Laser Doppler Flowmetry for three hours. A 15-minute stable baseline recording was obtained before the administration of saline or IRL-1620 1, 3, or 9 nmol/kg via the tail vein in a final volume of 0.2 ml and perfusion was recorded for three hours.

Selective Increase in the Accumulation of Paclitaxel in Breast Tumors

An experimental model of autochthonous rat mammary tumors was used for this study. Virgin female Sprague Dawley rats bearing mammary adenocarcinomas, 200-500 mm$^3$ in size, induced by N-methyl nitrosourea, were administered via tail vein with IRL-1620 at a dose of 3 nmol/kg followed by [$^3$H]paclitaxel, 15 minutes later. Animals were sacrificed three hours after the administration of [$^3$H]paclitaxel, and [$^3$H]paclitaxel was determined in the tumor and in various tissues by liquid scintillation counting of weighed tissue samples solubilized in tissue solubilizer and 10% glacial acetic acid (Rajeshkumar et al., 2005).

Figure 5:
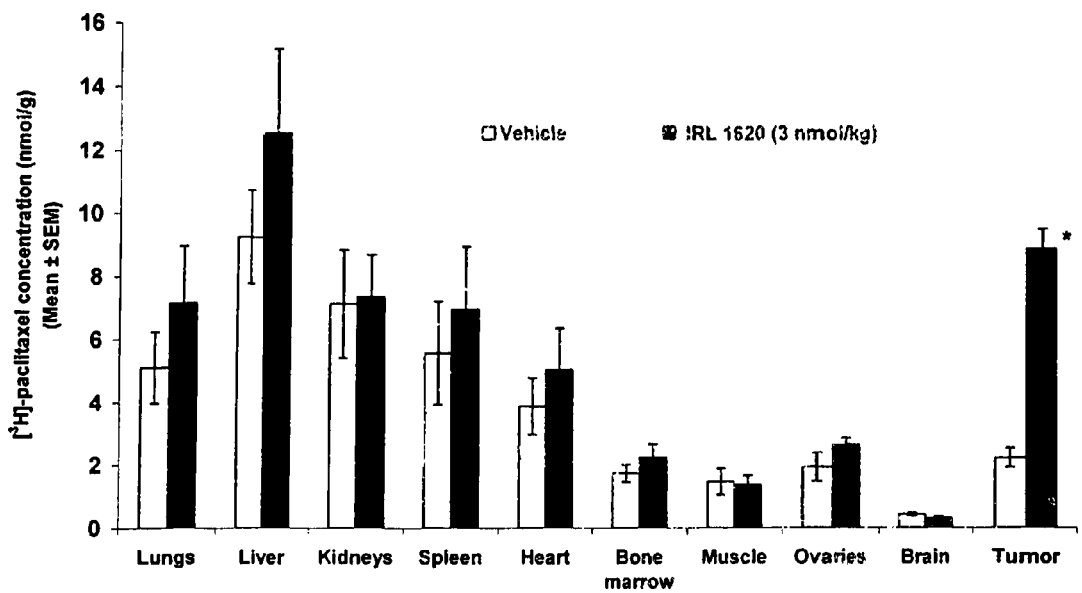
FIG. 5 contains bar graphs showing the effect of IRL-1620 on [$^3$H]paclitaxel concentrations in breast tumor and organs.

FIG. 5 shows the effect of IRL-1620 on [$^3$H]paclitaxel concentrations in breast tumor and organs (N=6/group). The animals were randomly grouped to receive saline or IRL-1620 (3 nmol/kg) via the tail vein in a final volume of 0.2 ml. Rats from each group received [$^3$H]paclitaxel:saline in a final volume of 1.0 ml (i.v.) 15 minutes after IRL-1620. Animals were sacrificed three hours after the administration of [$^3$H] paclitaxel. Tumor and organs were solubilized in tissue solubilizer and the concentration of [$^3$H]paclitaxel was determined using a liquid scintillation counter.

It is clear from the results presented in FIG. 5 that there was a three-fold increase in the accumulation of [$^3$H]paclitaxel in the tumor of rats treated with IRL-1620 compared to the vehicle-treated controls. There was no statistically significant increase in the accumulation of [$^3$H]paclitaxel in any of the other tissues studied in animals treated with IRL-1620, clearly demonstrating selectivity to tumor tissue. This technique of using an $ET_B$ receptor agonist to enhance the delivery of an imaging agent therefore has been demonstrated.

Studies in Prostate and Melanoma Animal Models

Figure 6:
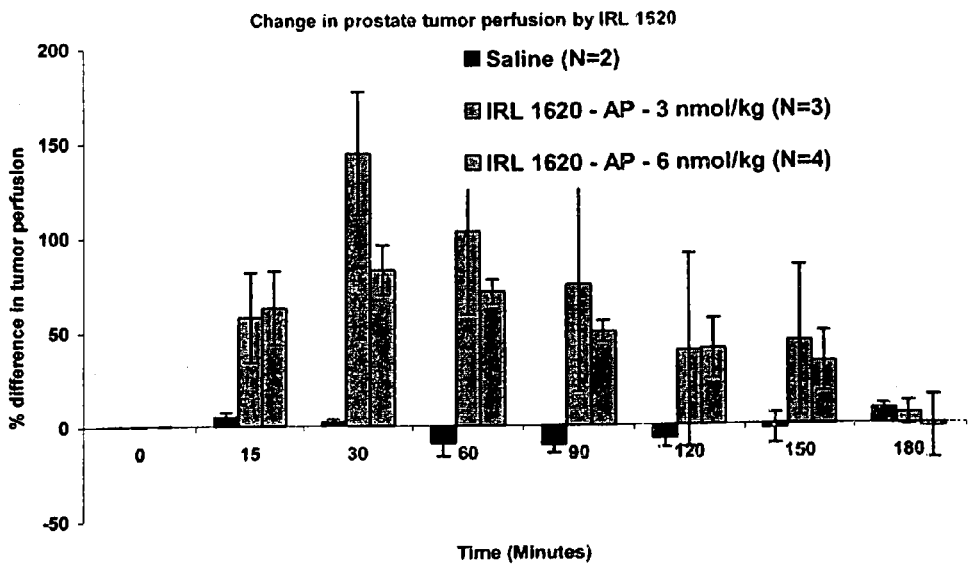
FIG. 6 contains bar graphs showing the percent difference in tumor blood perfusion in Copenhagen rats bearing prostatic tumors measured using Laser Doppler Flowmetry.

Prostate Tumor:

Male Copenhagen rats bearing prostate tumors, about 200 mm$^3$ in size, formed by intradermal injection of JHU-4 cells, were administered IRL-1620 at the dose of 3 and 6 nmol/kg via tail vein, and blood flow to the tumor was studied by Laser Doppler Flowmetry. As in the case of breast tumors, IRL-1620 enhanced blood supply to the prostate tumor within 15 minutes and the effect lasted for about 3 hours (FIG. 6). FIG. 6 shows the percent difference in tumor blood perfusion in Copenhagen rats bearing prostate tumors measured using Laser Doppler Flowmetry. IRL-1620 produced a significant increase in tumor blood perfusion compared to saline.

A biodistribution study also was performed in Copenhagen rats bearing prostate tumors, about 200 mm$^3$ in size, formed by intradermal injection of JHU-4 cells. [$^{14}$C]-Doxorubicin was administered to tumor bearing animals 15 minutes after saline or IRL-1620. Animals were scarified two hours after [$^{14}$C]-doxorubicin administration. Tumor and major organs were excised, weighed and solubilized in tissue solubilizer and radioactivity was measured. Results show that treatment with IRL-1620 produced a significant increase in accumulation of doxorubicin the tumor, while other organs were not significantly affected (FIG. 7).

Figure 7:
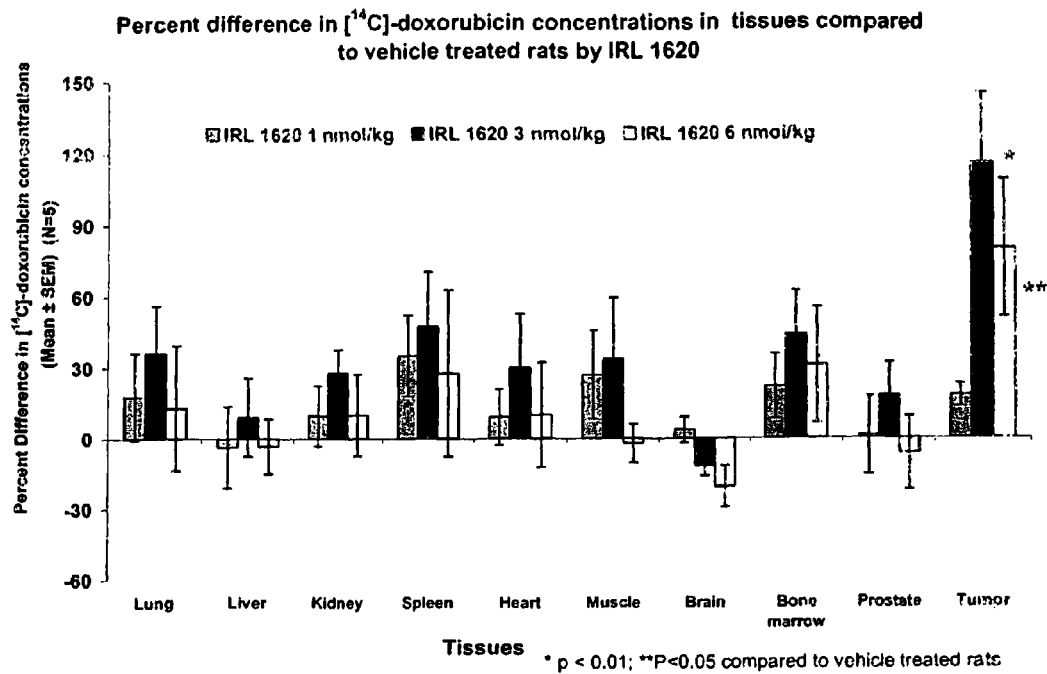
FIG. 7 contains bar graphs showing the percent difference in concentration of doxorubicin in prostate tumor-bearing rats treated with varying doses of IRL-1620.

FIG. 7 shows the percent difference concentration of doxorubicin in prostate tumor-bearing rats treated with various doses of IRL-1620. IRL-1620 (3 nmol/kg) dose produced the maximal increase in accumulation of doxorubicin in the tumor. Other organs were not affected.

These studies provide evidence of another compound that can be selectively delivered to the tumor, while other organs are not affected. Similarly, an imaging agent when injected after an $ET_B$ receptor agonist will be delivered selectively to the tumor producing better images of the tumor.

Figure 8:
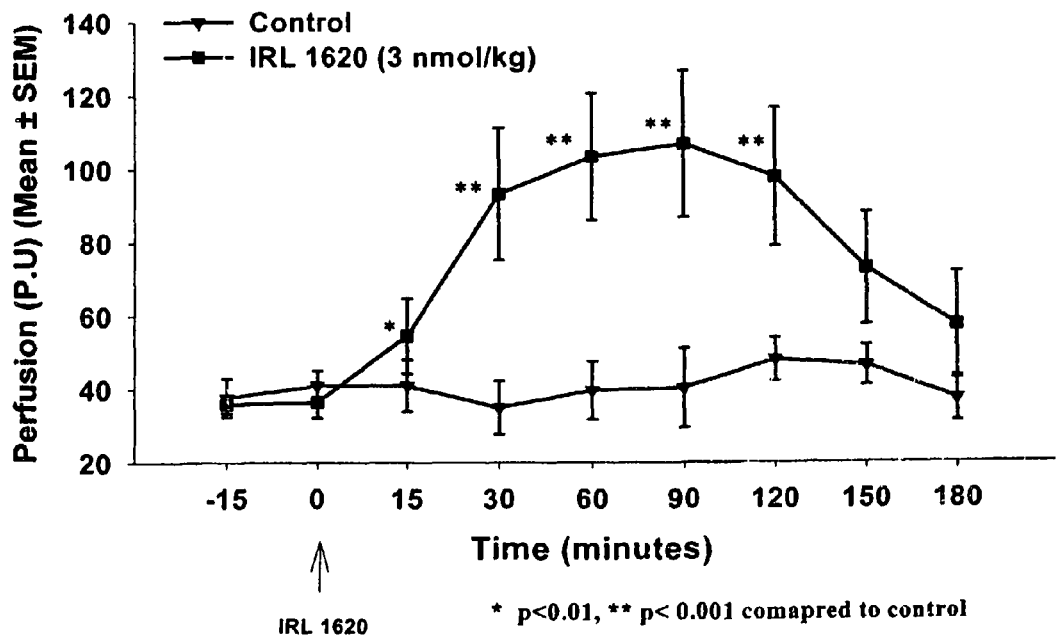
FIG. 8 contains plots showing the effect of IRL-1620 (3 nmol/kg) on melanoma tumor perfusion in nude mice.

Melanoma:

In another study, nude mice (N=4) were subcutaneously inoculated with one million human melanoma cells (UISO-MEL-2). Mice having a tumor volume of 200-400 mm$^3$ were treated with saline or IRL-1620 (3 nmol/kg, i.v), and perfusion was measured using a Periflux PF2b 4000 Laser Doppler Flowmetry for 180 minutes (FIG. 8).

Figure 9:
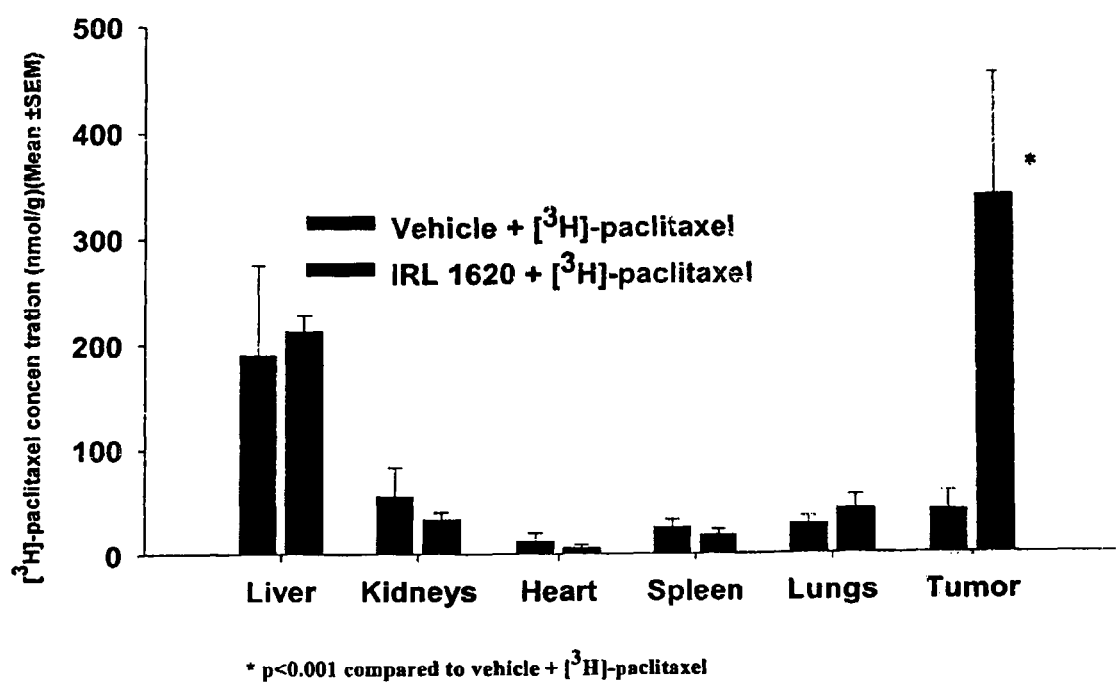
FIG. 9 contains bar graphs showing the effect of IRL-1620 (3 nmol/kg) on [$^3$H]paclitaxel concentration in melanoma tumor and tissues of nude mice.

A biodistribution study also was performed in human melanoma mice. [$^3$H]Paclitaxel 10 mCi/mice were administered to tumor bearing animals 15 minutes after saline or IRL-1620. Animals were scarified three hours after [$^3$H]paclitaxel administration. Tumor and major organs were excised, weighed and solubilized in tissue solubilizer and radioactivity was measured (FIG. 9).

$ET_A$ Receptor Antagonists Increase Tumor Blood Flow and can be Used in Better Imaging of Tumor A study using BMS182874, an $ET_A$ receptor antagonist, also was conducted. It was found that this compound also increased the tumor blood flow, and therefore can be used to enhance tumor images. A study using another $ET_A$ receptor antagonist, BQ123, found that tumor blood flow was significantly improved (Sonveaux et al., *Cancer Res.*, 64(9):3209-14 (2004)), and can be used to enhance delivery of anticancer drugs to the tumor. However, the increase in tumor blood perfusion using $ET_A$ receptor antagonists was found to be about 25%, whereas an increase of more than 200% in tumor perfusion was observed using the $ET_B$ receptor agonist IRL-1620. Because both classes of drugs can increase tumor blood flow selectively, they can enhance tumor images by using imaging agent for various techniques. It also is envisioned that $ET_B$ receptor agonists are preferred agents compared to $ET_A$ receptor antagonists to more effectively image the tumor.

Example Using an $ET_B$ Receptor Agonist or an $ET_A$ Receptor Antagonist in an Imaging Application A patient is prepared for intravenous drug administration by inserting a venous cannula. An $ET_B$ receptor agonist then is administered intravenously, and 15 minutes later an imaging agent is administered intravenously. An image then is taken using an appropriate instrument, e.g., X-ray, ultrasound, CT scan, or MRI, at various times following administration of the imaging agent. Images of the tumor are better visualized because the imaging agent is accumulated selectively in tumor tissue compared to normal tissues.

The above method also can be performed by administering an $ET_A$ receptor antagonist intravenously, then administering an imaging agent intravenously, followed by taking an image using the appropriate instrument at various times following administration of the imaging agent. Images of the tumor again are better visualized because the imaging agent is accumulated selectively in tumor tissue compared to normal tissues.

EXAMPLE

A patient is prepared for intravenous drug administration by inserting a venous cannula. An imaging agent then is administered, and an image is taken using the appropriate instrument, e.g., X-ray, ultrasound, CT scan, or MRI, at various times following administration of the imaging agent. The imaging agent next is washed from the patient, then an $ET_B$ receptor agonist is administered to the patient intravenously. Fifteen minutes later, the imaging agent again is administered, and a second image is taken using the appropriate instrument at various times following the second administration of the imaging agent. The images of the tumor in the presence and the absence of the $ET_B$ receptor agonist are compared. If the second images are brighter or more enhanced due to $ET_B$ receptor agonist administration, the tumor probably is malignant. Similarly, an $ET_A$ receptor antagonist can be used in place of an $ET_B$ receptor agonist to enhance the images of a tumor and determine the malignant or benign nature of the tumor.

Figure 10A:
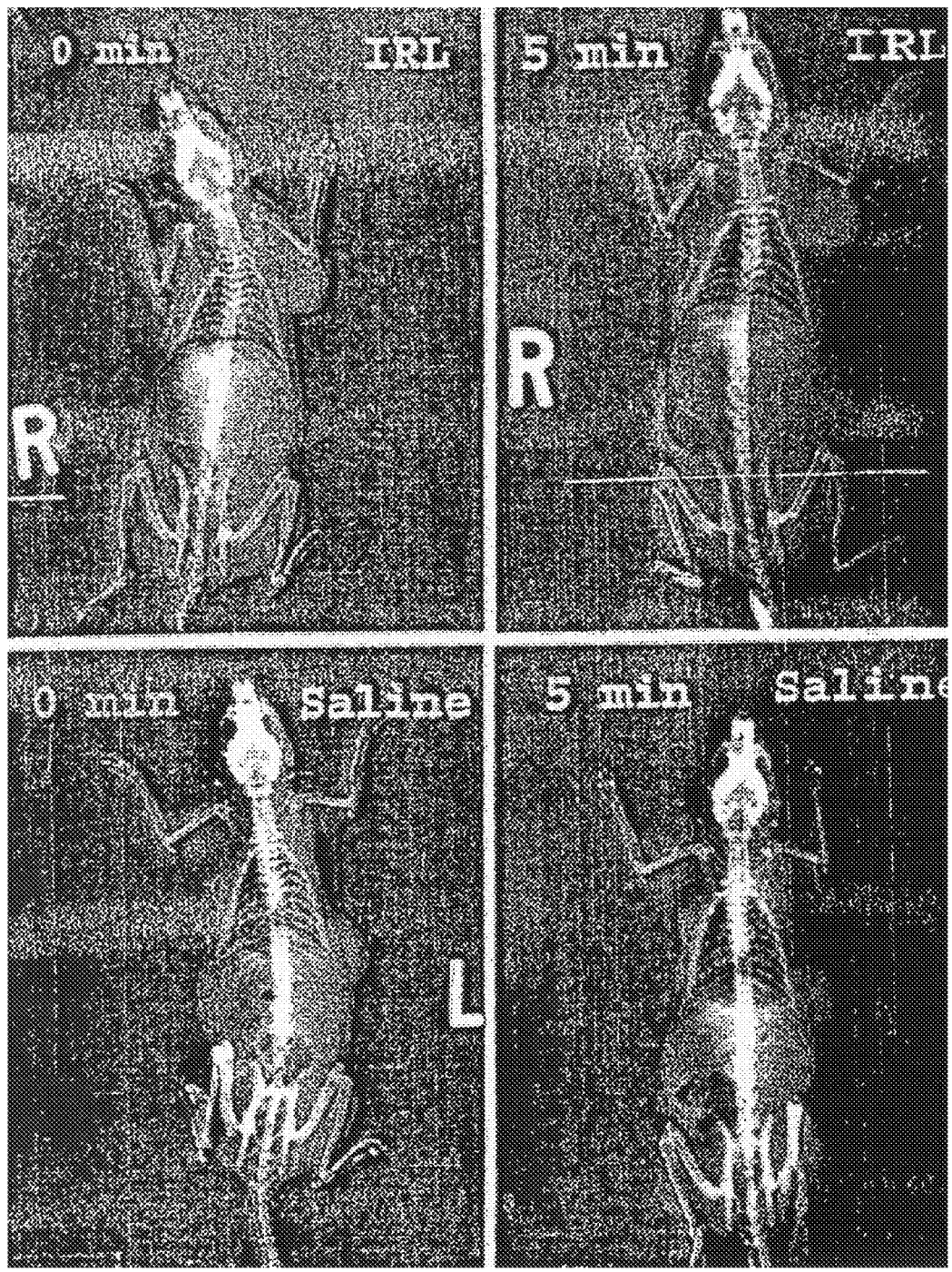
FIG. 10 contains X-rays of a rat having tumors and treated with an imaging agent in the presence and in the absence of an $ET_B$ receptor agonist. Images were taken at 0 and 5 minutes (FIG. 10A) and at 15 and 30 minutes (FIG. 10B) and represent increasing timepoints of the same rat.
Figure 10B:
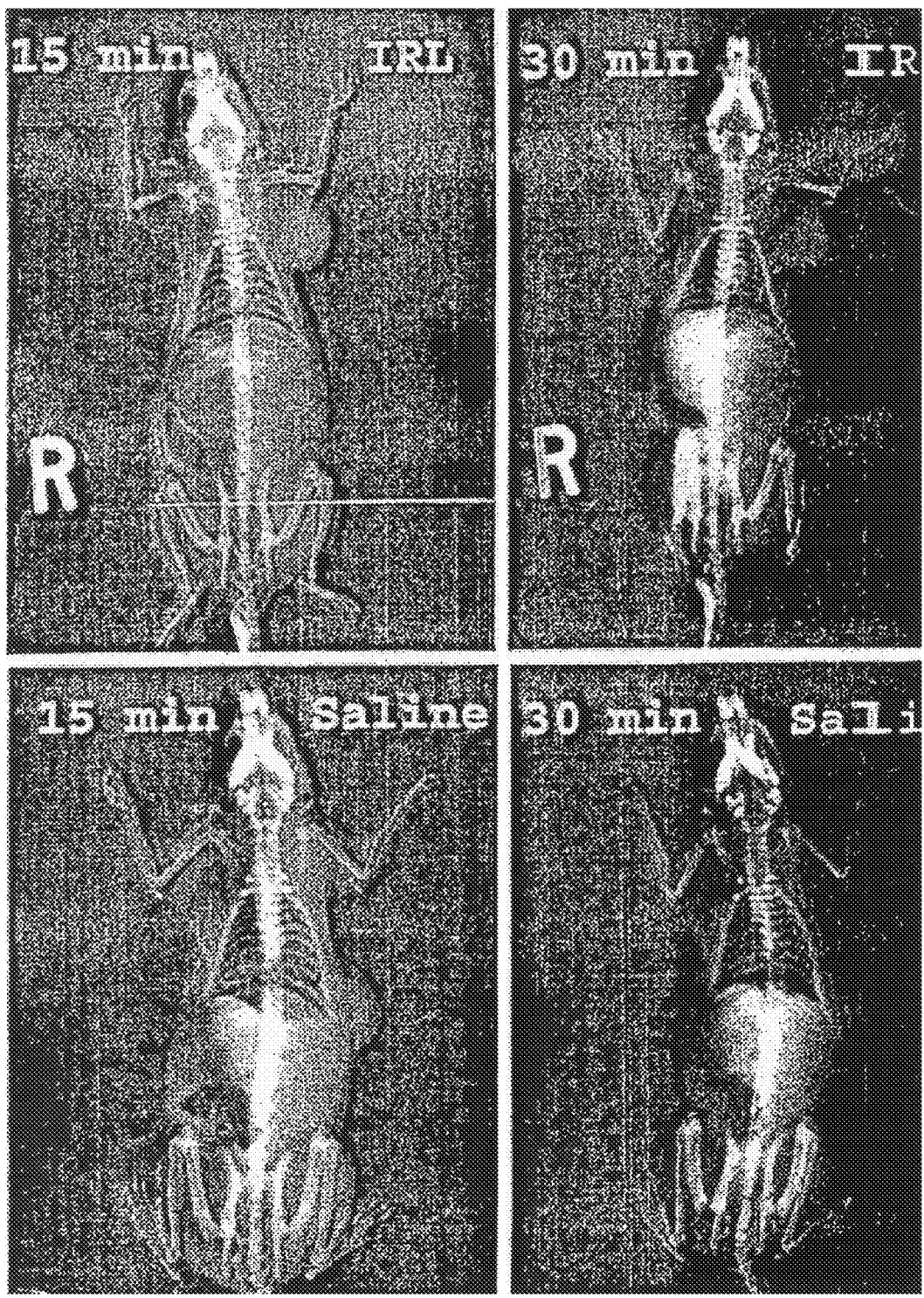

FIG. 10 also illustrates the present invention. The figure contains X-rays of a rat having tumors. One set of X-rays are of the rat administered an $ET_B$ receptor agonist (IRL) and an imaging agent (Hypaque). The other set of X-rays are of the rat administered saline and an imaging agent. FIG. 10 clearly shows that tumor visibility is increased 15 and 30 minutes after administration of an imaging agent and an $ET_B$ receptor agonist, while tumor visibility was not affected after administration of an imaging agent with saline (control).

Tumor blood vessels differ from normal host tissue blood vessels due to changes in the production of growth factors and vasoactive substances. As previously stated, endothelin is a known vasoactive substance that acts on two subtypes of receptors. $ET_A$ receptors, which are located on vascular smooth muscle cells, are responsible for vasoconstriction. $ET_B$ receptors, which are located on the endothelial cells, are responsible for vasodilation. Blood vessels in the growing part of tumors are devoid of smooth muscle covering, and tumor tissues have augmented $ET_B$ receptors compared to healthy host tissues. The above tests show that exogenous infusion of an $ET_B$ receptor agonist, e.g., ET-1 or IRL-1620, lead to a transient increase in the breast tumor perfusion by stimulating $ET_B$ receptors without altering perfusion to major organs.

The $ET_A$ receptor antagonist, $ET_B$ receptor agonist, and imaging agent (hereafter collectively "active ingredients") can be formulated in suitable excipients for administration. Such excipients are well known in the art. The active ingredients typically are present in such a composition in an amount of about 0.1% to about 75% by weight.

Pharmaceutical compositions containing the active ingredients are suitable for administration to humans or other mammals. Typically, the pharmaceutical compositions are sterile, and contain no toxic, carcinogenic, or mutagenic compounds that would cause an adverse reaction when administered.

A method of the present invention can be accomplished using active ingredients as described above, or as a physiologically acceptable salt, derivative, prodrug, or solvate thereof. The active ingredients can be administered as the neat compound, or as a pharmaceutical composition containing either or both entities.

The active ingredients can be administered by any suitable route, for example by oral, buccal, inhalation, sublingual, rectal, vaginal, intracisternal through lumbar puncture, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

The pharmaceutical compositions include those wherein the active ingredients are administered in an effective amount to achieve their intended purpose. More specifically, an "effective amount" means an amount effective to detect a tumor. Determination of an effective amount is well within the capability of those skilled in the art, especially in light of the detailed disclosure provided herein.

It is expected that, by administering an $ET_B$ receptor agonist or an $ET_A$ receptor antagonist in combination with an imaging agent, the amount of imaging agent can be decreased without decreasing the sensitivity of the diagnostic method, or the amount of imaging agent can be maintained at an unreduced level and the sensitivity of the diagnostic method will be increased, i.e., previously undetectable tumors can be detected.

The exact formulation, route of administration, and dosage of active ingredients are determined by an individual physician in view of the patient's condition. Dosage amount can be adjusted individually to provide levels of the active ingredients that are sufficient to detect the tumor of interest.

The amount of pharmaceutical composition administered is dependent on the subject being treated, on the subject's weight, the manner of administration, and the judgment of the prescribing physician.

Specifically, for administration to a human, oral dosages of active ingredients, individually generally are about 10 to about 200 mg daily for an average adult patient (70 kg). Thus, for a typical adult patient, individual tablets or capsules contain about 0.1 to about 50 mg active ingredients, in a suitable pharmaceutically acceptable vehicle or carrier. Dosages for intravenous, buccal, or sublingual administration typically are about 0.1 to about 100 μg/kg per dose. In practice, the physician determines the actual dosing that is most suitable for an individual patient, and the dosage varies with the age, weight, and response of the particular patient. The above dosages are exemplary of the average case, but there can be individual instances in which higher or lower dosages are merited, and such are within the scope of this invention.

The active ingredients can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active ingredients into preparations which can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When an effective amount of the active ingredients are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active ingredients, and preferably from about 25% to about 90% active ingredients. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active ingredients, and preferably about 1% to about 50% of active ingredients.

When a therapeutically effective amount of the active ingredients is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to an isotonic vehicle.

Suitable active ingredients can be readily combined with pharmaceutically acceptable carriers well known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active ingredients with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active ingredients can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the active ingredients can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active ingredients also can be formulated in rectal compositions, such as suppositories or retention enemas, e.g., containing conventional suppository bases. In addition to the formulations described previously, the active ingredients also can be formulated as a depot preparation. Such long-acting formulations can be administered by implantation (for example, subcutaneously or intramuscularly) or by intramuscular injection. Thus, for example, the active ingredients can be formulated with suitable polymeric or hydrophobic materials (for example, as an emulsion in an acceptable oil) or ion exchange resins, or as sparingly soluble derivatives, for example, as a sparingly soluble salt.

In particular, the active ingredients can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The active ingredients also can be injected parenterally, for example, intravenously, intramuscularly, subcutaneously, or intracoronarily. For parenteral administration, the active ingredients are best used in the form of a sterile aqueous solution which can contain other substances, for example, salts, or monosaccharides, such as mannitol or glucose, to make the solution isotonic with blood.

For veterinary use, the active ingredients are administered as a suitably acceptable formulation in accordance with normal veterinary practice. The veterinarian can readily determine the dosing regimen and route of administration that is most appropriate for a particular animal.

As stated above, it has been discovered that using an $ET_B$ receptor agonist or an $ET_A$ receptor antagonist, together with an imaging agent, enhances the ability of the imaging agent to detect a tumor in a mammal. The present method allows detection of previously undetectable tumors, thereby improving the ability to diagnose a cancer, allowing a cancer treatment to begin earlier, and improving the probabilities of a recovery from the cancer. The present method also allows for a more accurate determination of the progress of a cancer treatment regimen. The present method also can be used for staging of cancer.

The imaging agent, like the $ET_B$ receptor agent or $ET_A$ receptor antagonist, is administered in an effective amount to perform its intended function. The imaging agent can be administered by any suitable means, typically using a composition containing the imaging agent.

The imaging agent can be administered simultaneously with the $ET_B$ receptor agonist or $ET_A$ receptor antagonist, or prior to or after $ET_B$ receptor agonist or $ET_A$ receptor antagonist administration.

REFERENCES

1. A. Rai et al., *Cancer Chemother. Pharmacol.*, 51(1): 21-8 (2003);
2. A. Gulati et al., *J. Cardvasc. Pharmacol.*, in press, (2004);
3. A. Rai et al., 2004 Pharmaceutics and Drug Delivery Conference, Philadelphia, Pa., Jun. 7-9, 2004;
4. J. Folkman, *Cancer Res.*, 46(2): 467-73 (1986);
5. P. Lissoni et al., *J. Biol. Regul. Homeost. Agents*, 15(2): 140-4 (2001);
6. J. Mattsson et al., Tumor vessel innervation and influence of vasoactive drugs on tumor blood flow. Boca Raton: CRC Press (1979), (H. Peterson, ed., Tumor Blood Circulation);
7. H. S. Reinhold, In vivo observations of tumor blood flow. Boca Raton: CRC Press (1979), (H. Peterson, ed., Tumor Blood Circulation);
8. B. A. Warren, The vascular morphology of tumors. Boca Raton: CRC Press (1979), (H. Peterson, ed., Tumor Blood Circulation);
9. T. F. Luscher et al., The endothelium: modulator of cardiovascular function. Boca Raton: CRC Press (1990);
10. J. F. Secombe et al., Vasoactive factors produced by the endothelium. Austin: Landes (1994);
11. T. Sakurai et al., *Nature*, 348(6303): 732-5 (1990);
12. A. Inoue et al., *Proc. Natl. Acad. Sci. USA*, 86(8): 2863-7 (1989);
13. A. Gulati et al., *Gen. Pharmacol.*, 26(1): 183-93 (1995);
14. G. Helmlinger et al., *Nature*, 405(6783): 139-41 (2000);
15. P. Carmeliet et al., *Nature*, 407(6801): 249-57 (2000);
16. R. K. Jain, *Adv. Drug Deliv. Rev.*, 46(1-3): 149-68 (2001);
17. Y. S. Chang et al., *Proc. Natl. Acad. Sci. USA*, 97(26): 14608-13 (2000);
18. A. E. Rogers et al., Chemically induced mammary gland tumors in rate: modulation by dietary fat. New York: Alan R. Liss, Inc. (1986); (C. Ip et al., eds., Dietary Fat and Cancer).
19. D. Macejova et al., *Endocr. Regul.*, 35(1): 53-9 (2001);
20. M. J. van Zeieten, The rat as animal model in breast cancer research. Boston: Martinus Nijhoff Publishers (1984);
21. E. B. Astwood et al., *Am. J. Anat.*, 61(372) (1937);
22. I. H. Russo et al., *J. Natl. Cancer Inst.*, 61(6): 1439-49 (1978);
23. C. W. Song et al., *Int. J. Radiat. Oncol. Biol. Phys.*, 18(4): 903-7 (1990);
24. C. W. Song et al., *Int. J. Radiat. Oncol. Biol. Phys.*, 17 (5): 1041-7 (1989);
25. M. Yanagisawa et al., *J. Hypertens. Suppl.* 6(4): S188-91 (1988);
26. S. Hori et al., *Endocrinology*, 130(4): 1885-95 (1992);
27. H. Arai et al., *Nature*, 348(6303): 730-2 (1990);
28. T. Kuwaki et al., *Jpn. J. Physiol.*, 40(6): 827-41 (1990);
29. K. M. Bell et al., *J. Cardiovasc. Pharmacol*, 26(*Suppl* 3): S222-5 (1995).

Modifications and variations of the invention as hereinbefore set forth can be made without departing from the spirit and scope thereof, and, therefore, only such limitations should be imposed as are indicated by the appended claims.

APPENDIX A

Balanced $ET_A/ET_B$ Antagonists

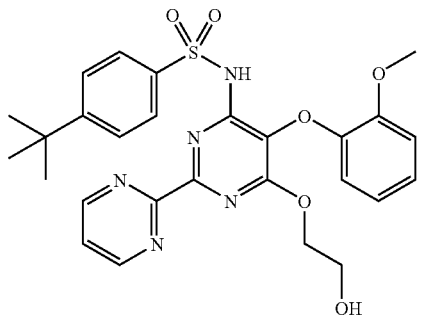

bosentan

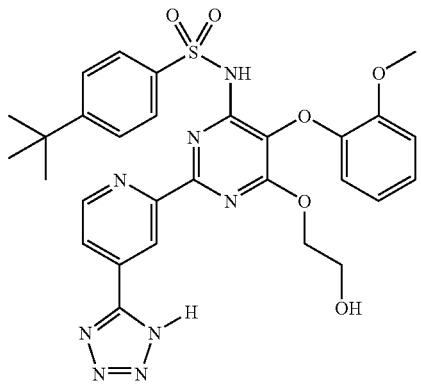

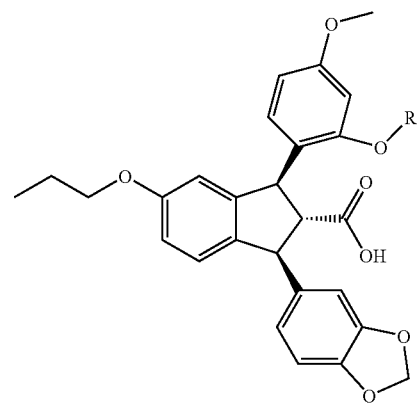

3 R = CH$_2$CO$_2$H SB209670
4 R = CH$_2$CH$_2$OH SB217242

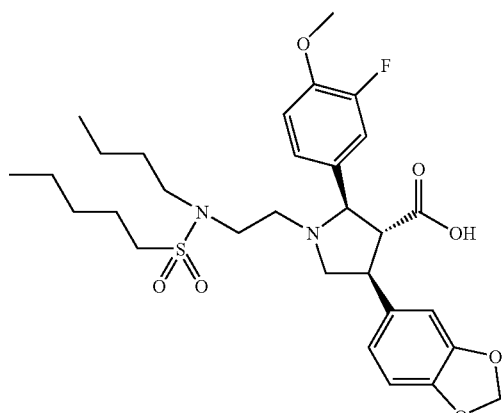
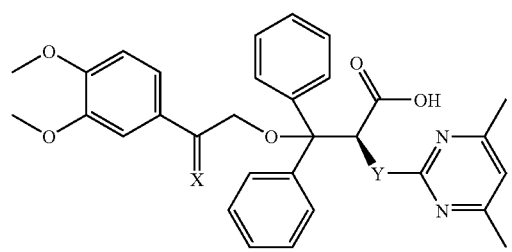
6 X = H₂, Y = CH₂ S-LU 302872
7 X = O, Y = O
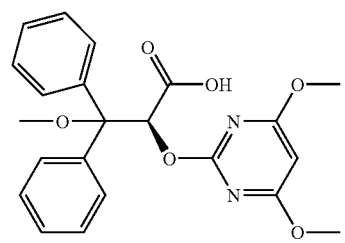
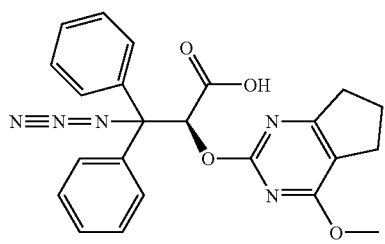
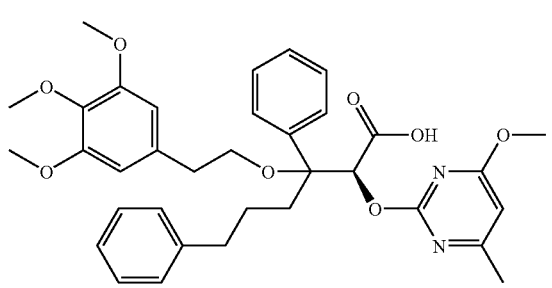
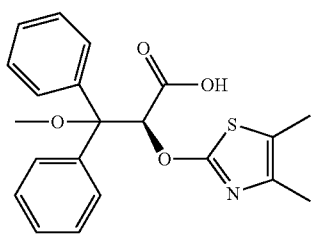
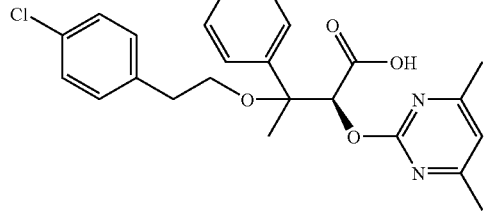
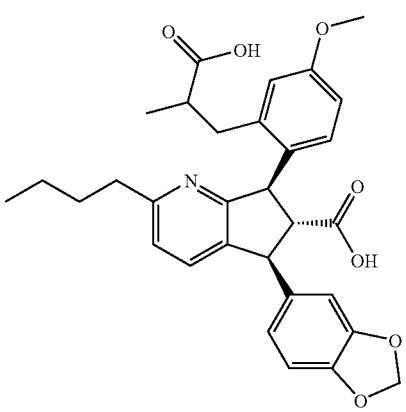
J-104132
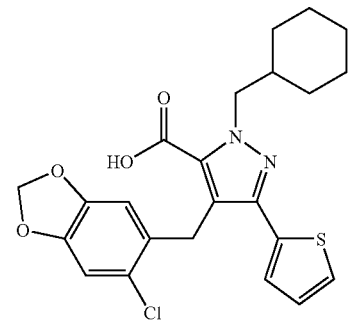
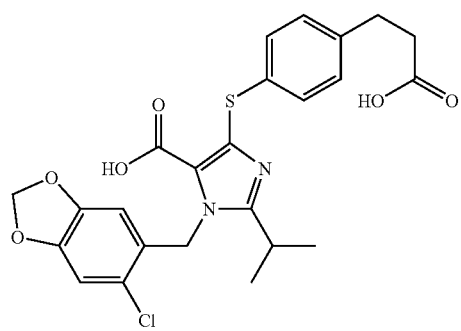

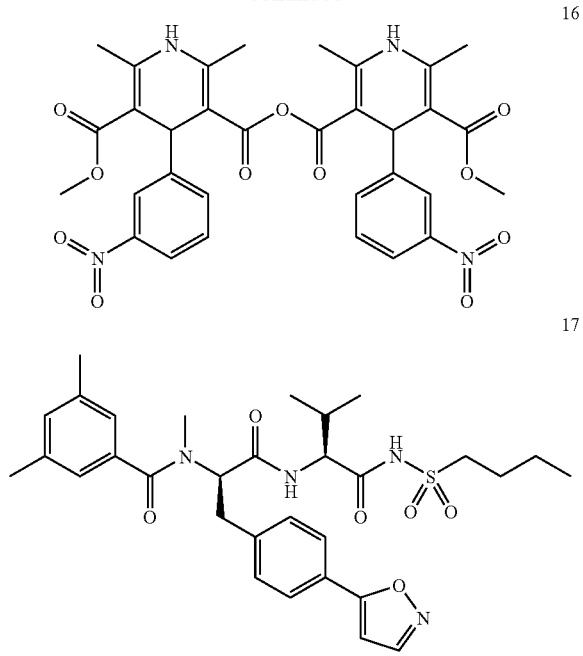
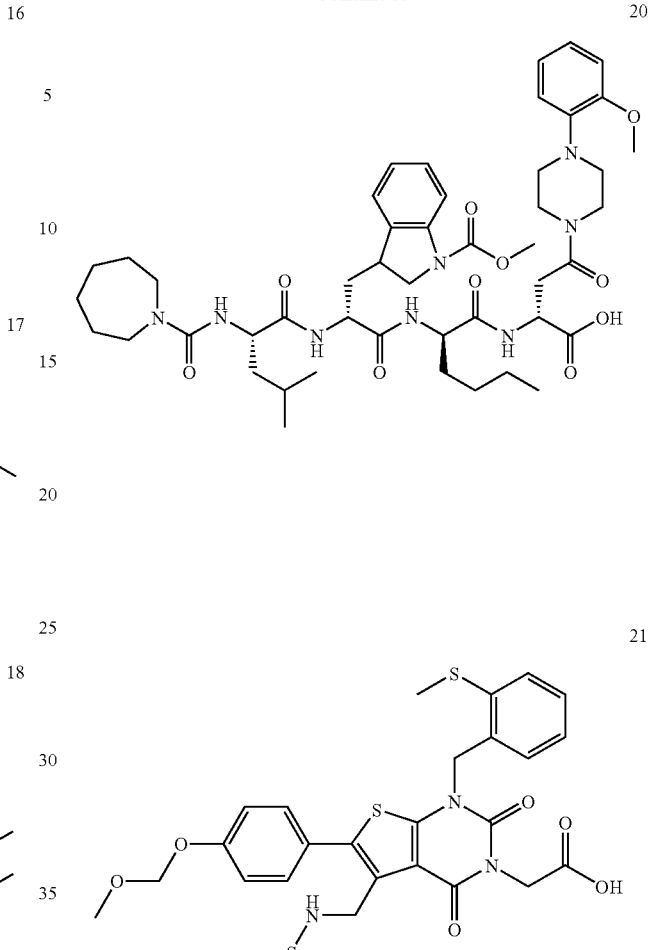
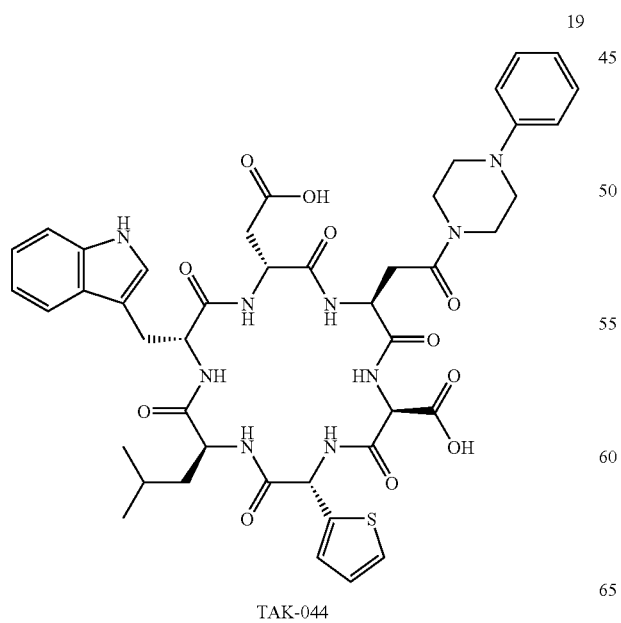
TAK-044

APPENDIX B
Miscellaneous ET Antagonists
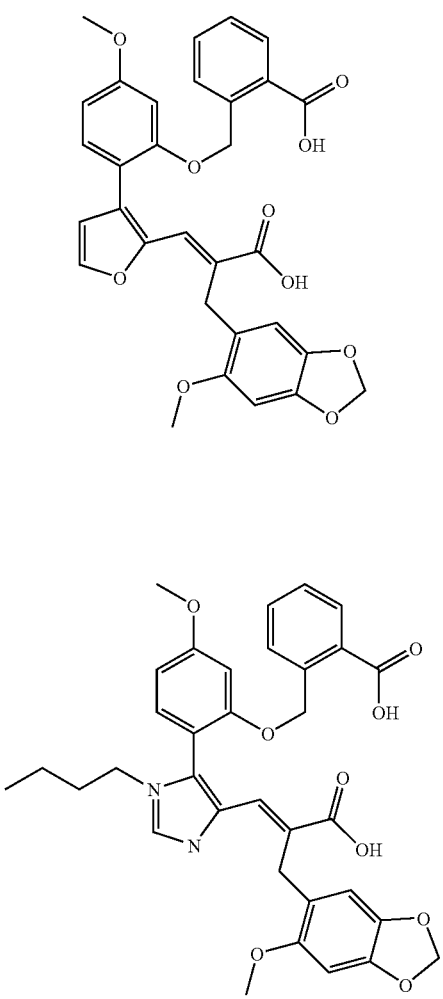
33
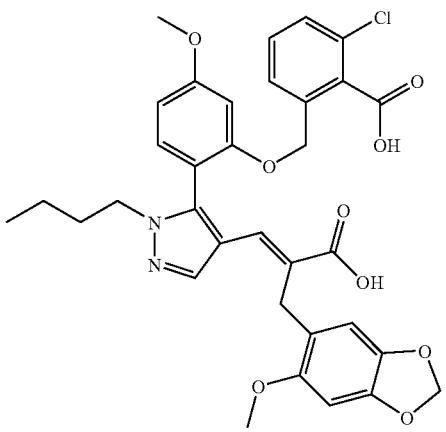
36
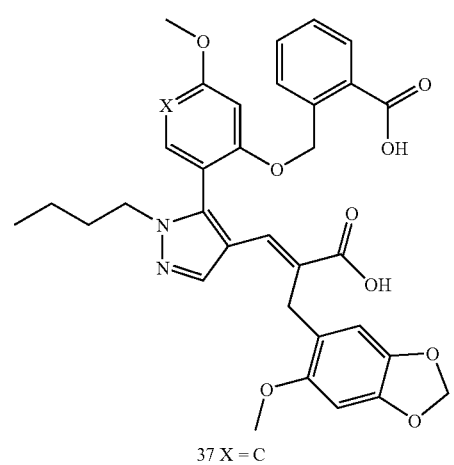
37 X = C
38 X = N
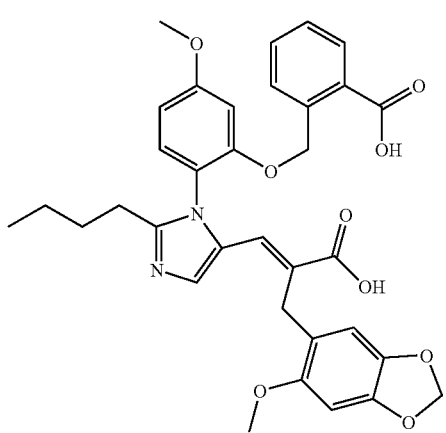
35
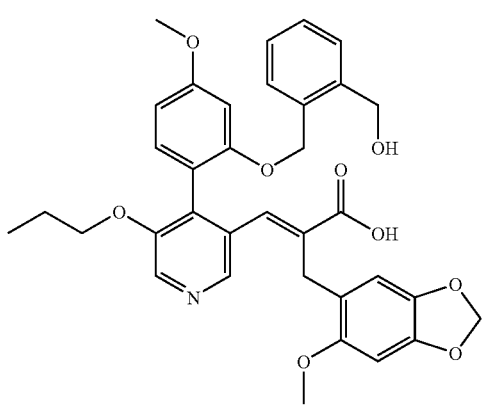
39

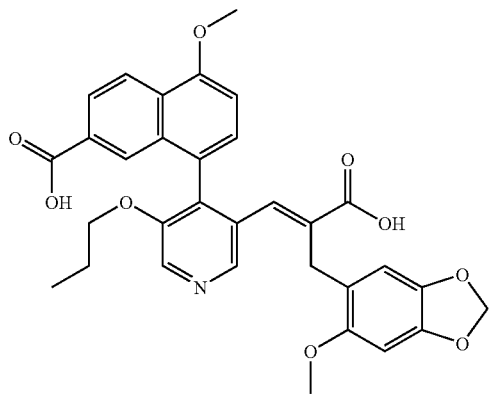
40
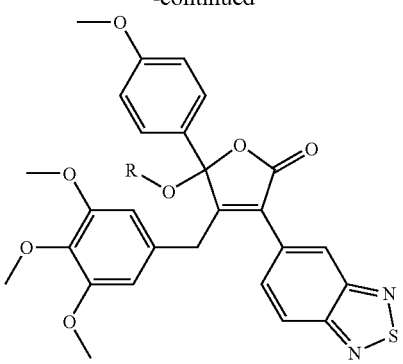
44 R = H
45 R = CONHCH$_2$CO$_2$C$_2$H$_5$
41
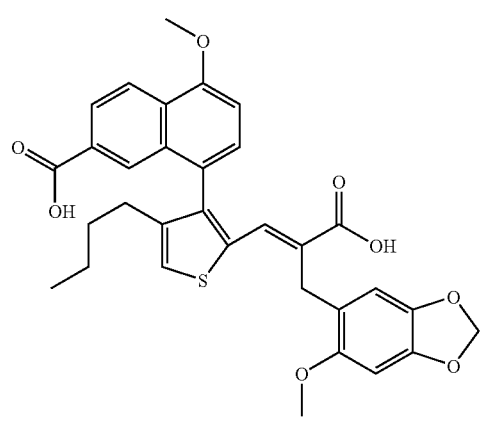
46
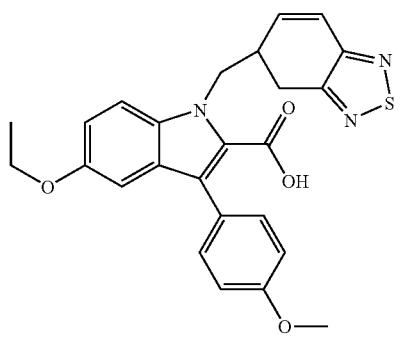
42
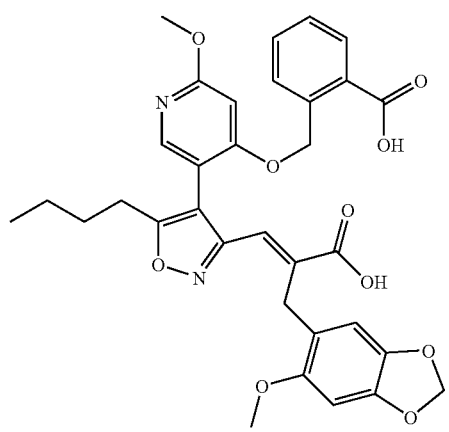
47
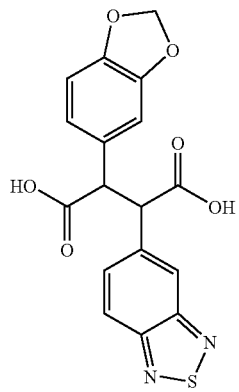
43
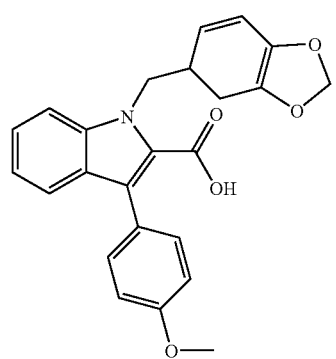
48
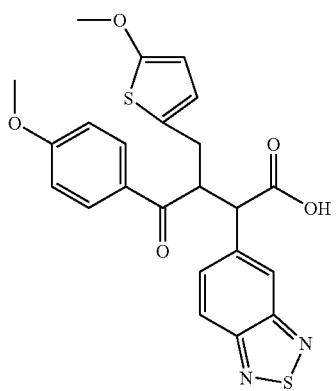

49
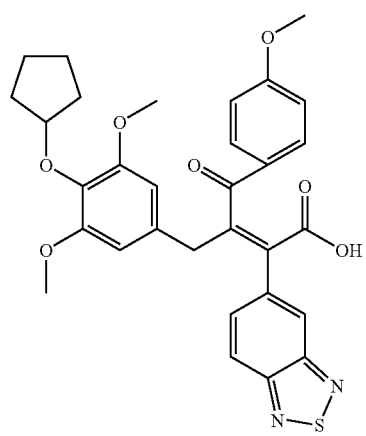
50
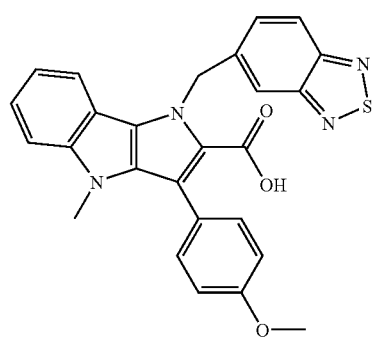
51
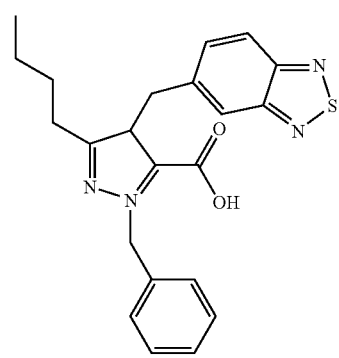
52
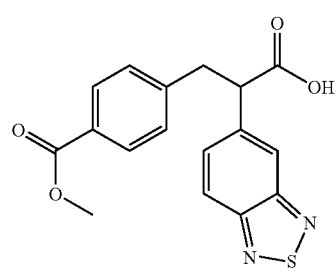
53
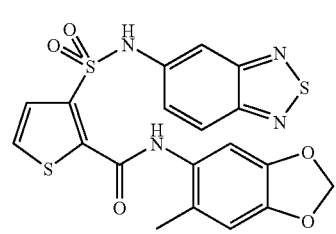
54
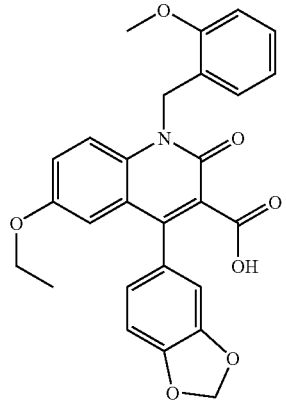
55
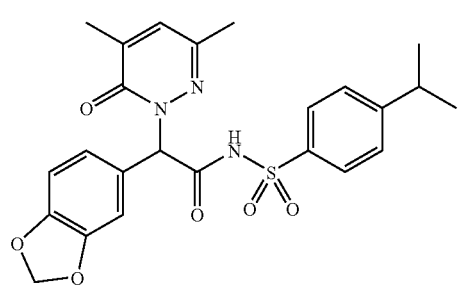
56
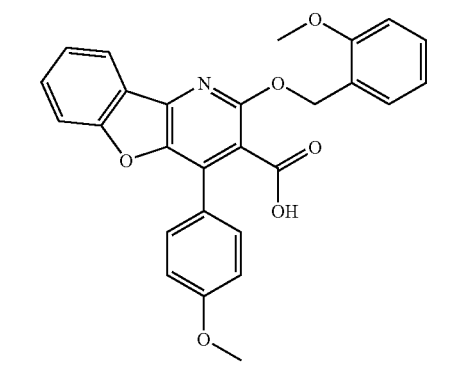
57
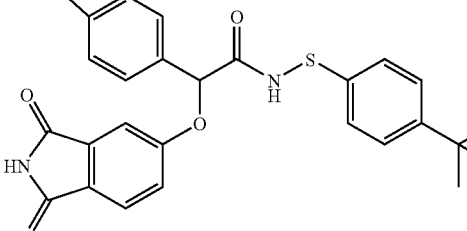
58
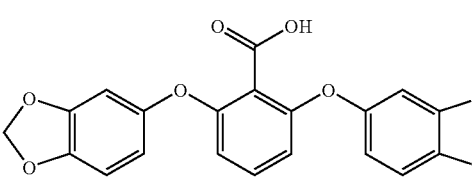

29
-continued
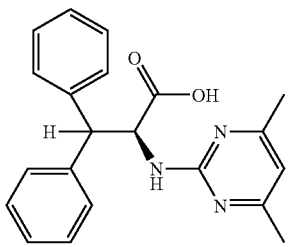
59
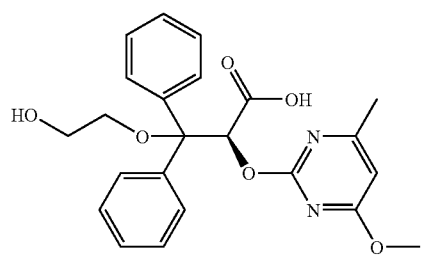
60
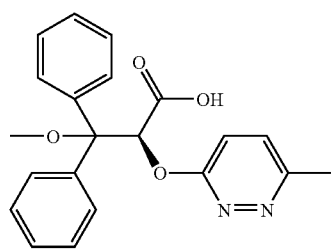
61
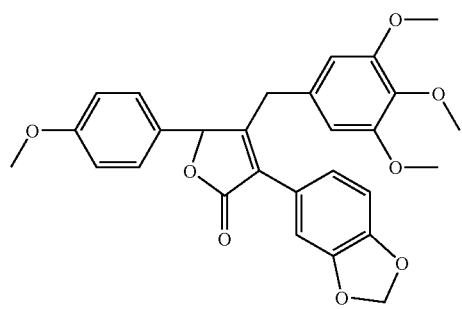
62
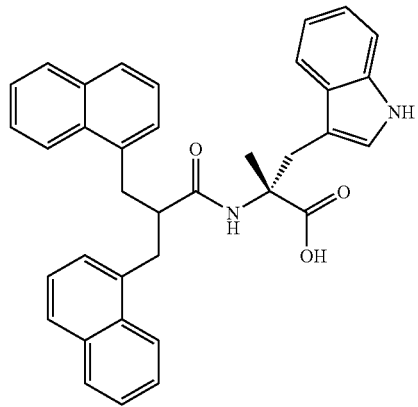
63
30
-continued
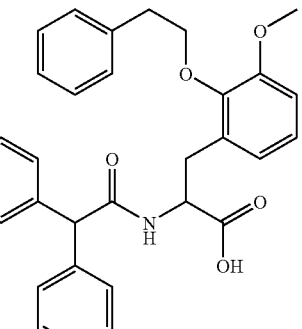
64
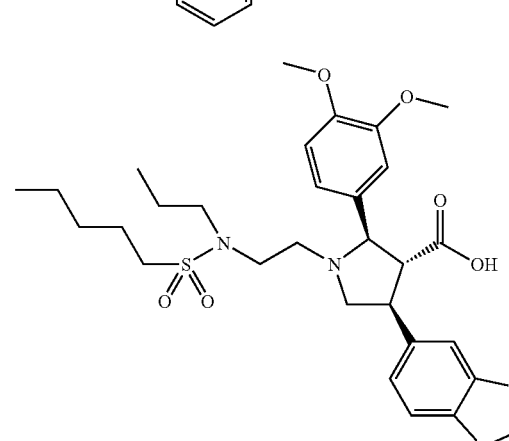
65
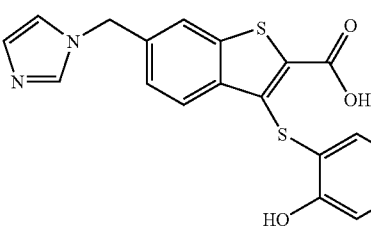
66
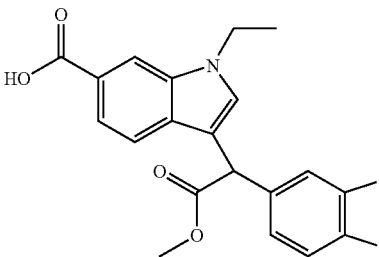
67
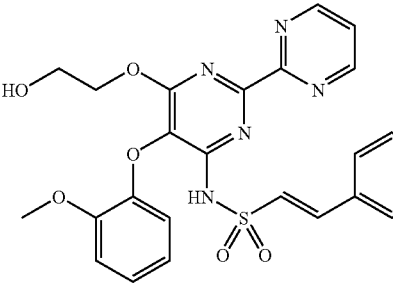
68

-continued

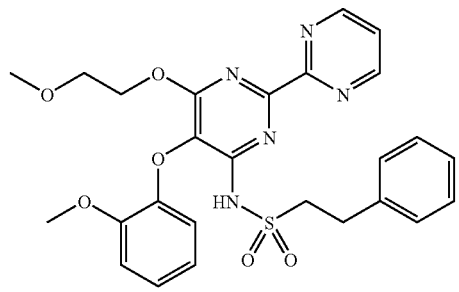
69

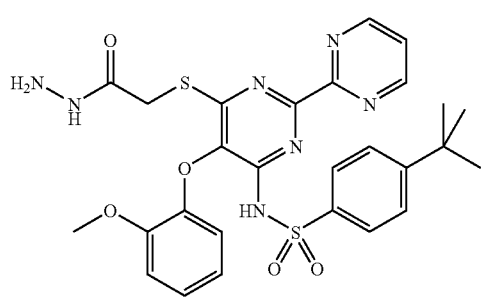
70

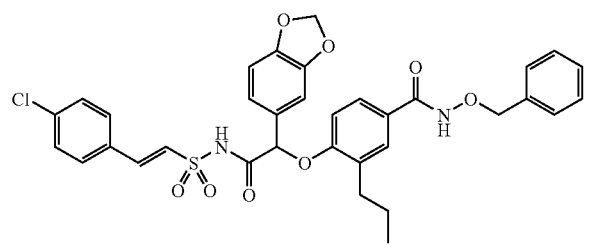
71

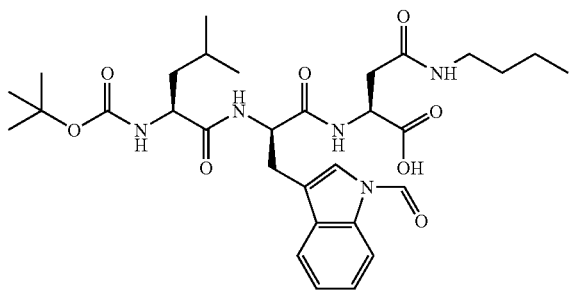
72

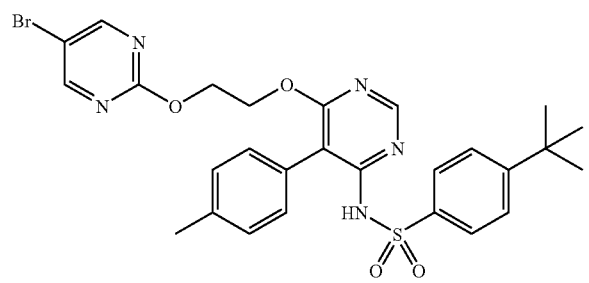
73

-continued

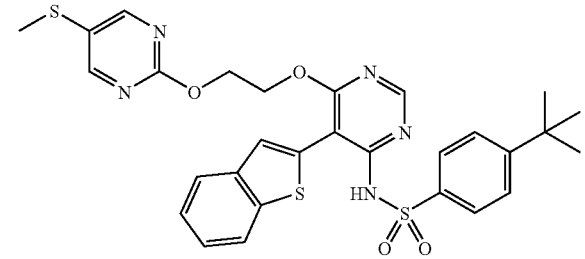
74

What is claimed is:

1. A method of differentiating a malignant tumor from a benign tumor in a mammal, the method comprising the steps, performed in order of (a) to (g), of
   (a) administering an imaging agent to the mammal;
   (b) obtaining a first image of the tumor using a diagnostic imaging procedure;
   (c) rinsing the imaging agent from the mammal;
   (d) administering an endothelin B receptor agonist to the mammal and then waiting about 15 minutes;
   (e) administering the imaging agent to the mammal;
   (f) obtaining a second image of the tumor using the diagnostic imaging procedure; and then
   (g) comparing the first image of step (b) to the second image of step (e), wherein, when the second image is enhanced compared to the first image, the tumor is malignant.

2. The method of claim 1 wherein the malignant tumor or the benign tumor is associated with a cancer selected from the group consisting of ovarian cancer, colon carcinoma, breast cancer, brain cancer, liver cancer, colorectal cancer, metastatic colorectal cancer, metastatic breast cancer, esophageal cancer, gastric cancer, small bowel cancer, hepatobiliary cancer, pancreatic cancer, lymphoma, bladder cancer, germ cell/testicular tumors, kidney cancer, prostate cancer, genitourinary cancer, head and neck cancer, nonsmall cell lung cancer, small cell lung cancer, other lung cancers, melanoma, and pediatric solid tumors.

3. The method of claim 1 wherein the endothelin B receptor agonist is selected from the group consisting of ET-1, ET-2, ET-3, BQ3020, IRL-1620, sarafotoxin S6c, [Ala$^{1, 3, 11, 15}$]ET-1, and mixtures thereof.

4. The method of claim 3 wherein the endothelin B receptor agonist comprises IRL-1620.

5. The method of claim 1 wherein the imaging agent is selected from the group consisting of an X-ray contrast agent, an ionic contrast medium, a dimeric ionic contrast agent, an ioxaglic acid derivative, a nonionic contrast medium, a nonionic dimeric contrast medium, a magnetic resonance imaging contrast agent, superparamagnetic iron oxide particles, an ultrasound contrast agent, a nuclear imaging agent, a radioimmunopharmaceutical, a diagnostic radiopharmaceutical, a perfluorocarbon-containing contrast agent, bismuth nitrate, a nonionic monomeric X-ray contrast agent, fluorodeoxythymidine, 2'-fluoro-5-methyl-1-beta-D-arabinofuranosyluracil, and iodine-124 iodo-2'-deoxyuridine.

6. The method of claim 1 wherein the mammal is a human.

7. The method of claim 1 capable of detecting a tumor smaller in size than a tumor detectable using the imaging agent alone.

8. The method of claim 1 wherein the diagnostic imaging procedure is selected from the group consisting of computed tomography imaging, magnetic resonance imaging, mammography, nuclear medicine imaging, positron emission tomography, ultrasound imaging, and X-ray imaging.

\* \* \* \* \*